(12) United States Patent
Poyil et al.

(10) Patent No.: US 11,073,384 B2
(45) Date of Patent: Jul. 27, 2021

(54) SYSTEMS AND METHODS FOR MIXED LAYER DEPTHS

(71) Applicant: King Abdulaziz University, Jeddah (SA)

(72) Inventors: Abdulla Cheriyeri Poyil, Jeddah (SA); Mohammed Ali Alsaafani, Jeddah (SA); Turki Metabe Alraddadi, Jeddah (SA); Alaa Mohammed Albarakati, Jeddah (SA)

(73) Assignee: King Abdulaziz University, Jeddah (SA)

( * ) Notice: Subject to any disclaimer, the term of this patent is extended or adjusted under 35 U.S.C. 154(b) by 364 days.

(21) Appl. No.: 15/796,046

(22) Filed: Oct. 27, 2017

(65) Prior Publication Data
US 2019/0128668 A1    May 2, 2019

(51) Int. Cl.
| | |
|---|---|
| *G01B 21/18* | (2006.01) |
| *G01N 25/00* | (2006.01) |
| *G01N 9/00* | (2006.01) |
| *G01N 33/18* | (2006.01) |
| *G01N 9/36* | (2006.01) |

(52) U.S. Cl.
CPC ............ *G01B 21/18* (2013.01); *G01N 9/00* (2013.01); *G01N 25/00* (2013.01); *G01N 33/18* (2013.01); *G01N 33/1833* (2013.01); *G01N 9/36* (2013.01)

(58) Field of Classification Search
CPC ......... G01B 21/18; G01N 25/00; G01N 33/18
See application file for complete search history.

(56) References Cited

U.S. PATENT DOCUMENTS

| | | | |
|---|---|---|---|
| 6,771,563 B1 * | 8/2004 | Bernard ................ | E21B 19/002 367/131 |
| 2010/0082264 A1 | 4/2010 | Barron et al. | |
| 2013/0158871 A1 | 6/2013 | Helber et al. | |

OTHER PUBLICATIONS

Chu, Determination of Ocean Mixed Layer Depth from Profile Data, Proceedings on 15th Symposium on Integrated Observing and Assimilation Systems for the Atmosphere, Oceans and Land Surface (IOAS-AOLS), American Meteorological Society, Jan. 23-27, Seattle (Year: 2011).*

Arnon, A., N. G. Lensky, and J. S. Selker, High-resolution temperature sensing in the Dead Sea using fiber optics, Water Resour. Res., 50, 1756-1772 (Year: 2014).*

Kara, An optimal definition for ocean mixed layer depth, Journal of Geophysical Research, vol. 105, No. 07, pp. 16,803-16,821 Jul. 15, 2000.*

(Continued)

*Primary Examiner* — Michael J Dalbo
(74) *Attorney, Agent, or Firm* — Oblon, McClelland, Maier & Neustadt, L.L.P.

(57) ABSTRACT

A method for determining a mixed layer depth (MLD) in a body of water includes receiving a vertical high resolution profile corresponding to the body of water. Additionally, a profile segment corresponding to a portion of the profile between a surface of the body of water and a bottom of a thermocline is selected to be analyzed. Further, a depth within the profile segment corresponding to MLD is identified. For example, the MLD in Gulf of Aden is analyzed using vertical high resolution profiles of both temperature and density. The method produces MLD estimates for more than 95% of the profiles and overcomes major limitations of conventional methods.

4 Claims, 11 Drawing Sheets

(56) References Cited

OTHER PUBLICATIONS

Lorbacher, Ocean Mixed Layer Depth: A Subsurface Proxy of Ocean-Atmosphere Variability, The ECCO Report Series, No. 38, 61 Pages total, May 22, 2005.*

Chi, The surface mixed layer heat budget from mooring observations in the central Indian Ocean during Madden-Julian Oscillation events. J. Geophys. Res. Oceans, 119, 4638-4652, https://doi.org/10.1002/2014JC010192—Jul. 2014.*

Lorbacher, K., et al., "Ocean Mixed Layer Depth: A Subsurface Proxy of Ocean-Atmosphere Variability", The ECCO Report Series, No. 38, 61 Pages total, (May 22, 2005).

Houpert, L. et al, "Seasonal Cycle of the Mixed Layer, the Seasonal Thermocline and the Upper-Ocean Heat Storage Rate in the Mediterranean Sea Derived from Observations", Progress in Oceanography, vol. 132, pp. 333-352, (Dec. 13, 2014).

* cited by examiner

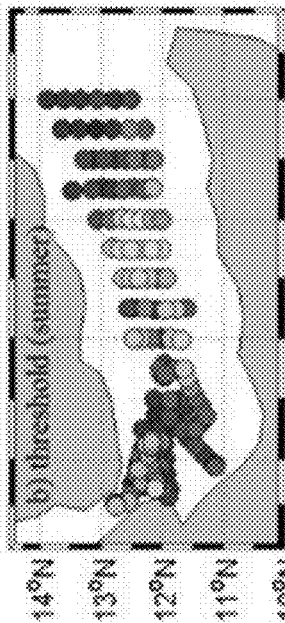
*Fig. 2A*
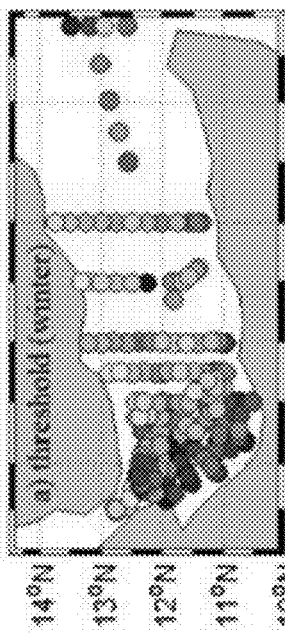
*Fig. 2B*
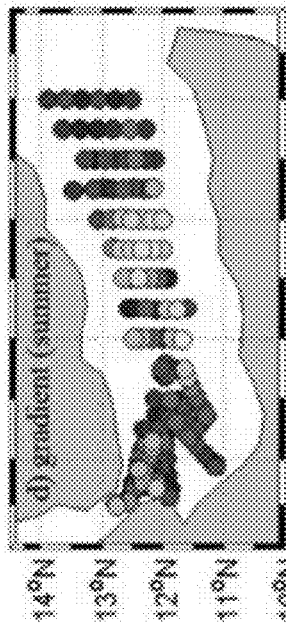
*Fig. 2C*
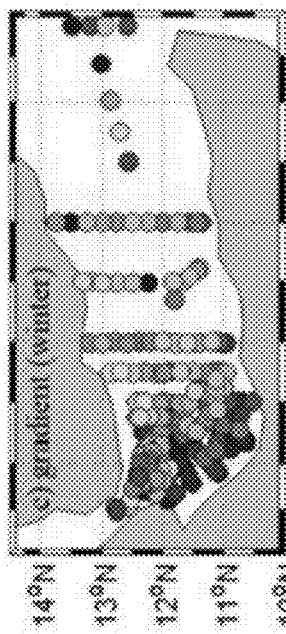
*Fig. 2D*
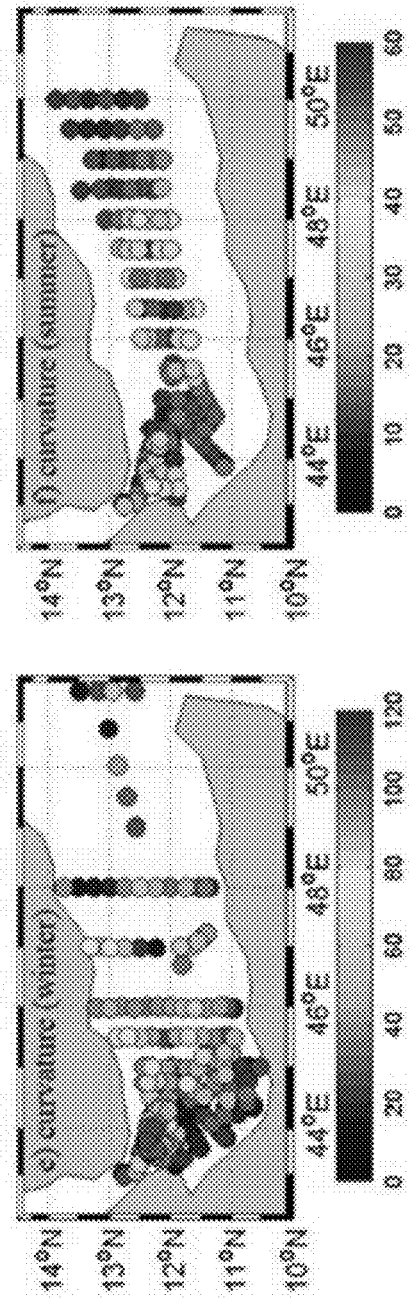
*Fig. 2E*
*Fig. 2F*

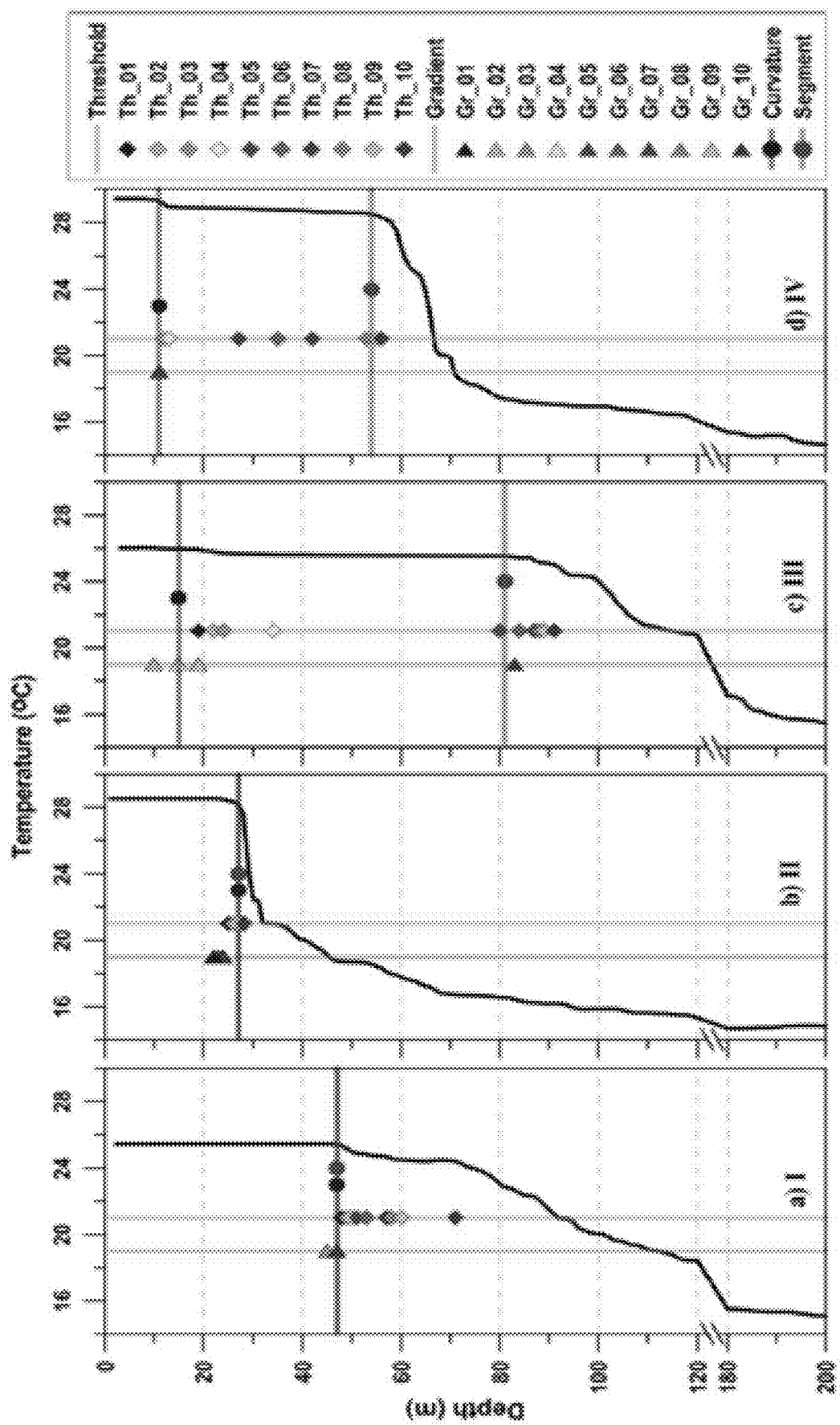

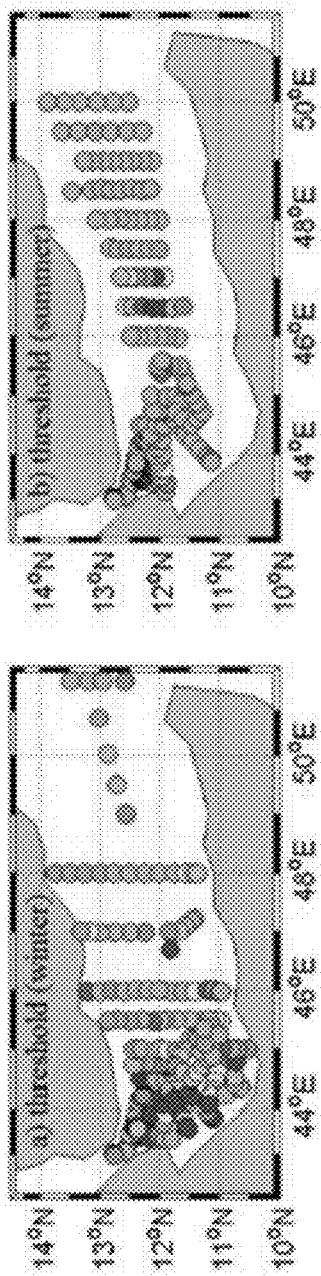
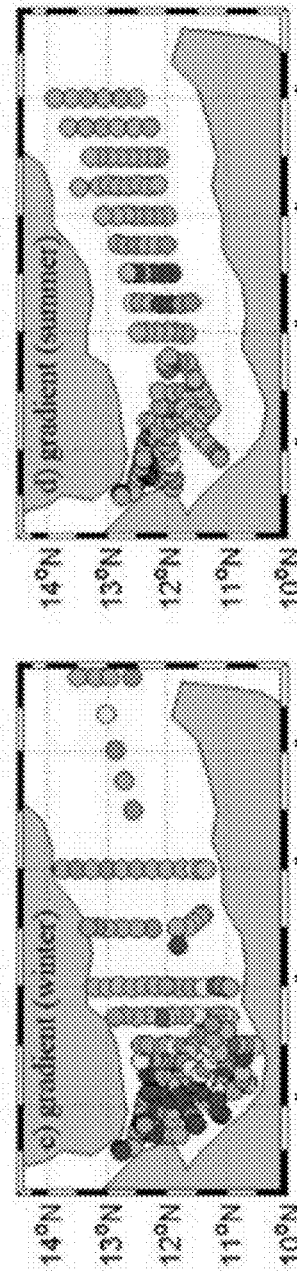
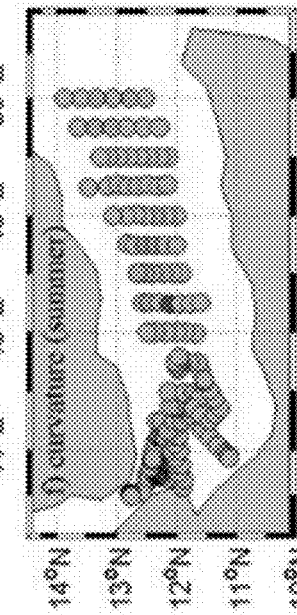
Fig. 4A Fig. 4B Fig. 4C Fig. 4D Fig. 4E Fig. 4F

SYSTEMS AND METHODS FOR MIXED LAYER DEPTHS

STATEMENT REGARDING PRIOR DISCLOSURES BY THE INVENTORS

Aspects of this technology are described in an article "Estimation of Mixed Layer Depth in the Gulf of Aden: A New Approach" by Abdulla C. P., M. A. Alsaafani, T. M. Alraddadi, A. M. Albarakati, in PLOS ONE|DOI:10.1371/journal.pone.0165136 Oct. 27, 2016, which is incorporated herein by reference in its entirety.

BACKGROUND OF THE INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Continuous energy transfer between atmosphere and ocean develops a quasi-uniform upper layer with nearly uniform temperature, salinity, and density. The depth of this layer (called mixed layer depth or MLD) is important as it determines the volume or mass of water over which flux from the atmosphere is distributed. See Cury P, Roy C. Optimal Environmental Window and Pelagic Fish Recruitment Success in Upwelling Areas. Can J Fish Aquat Sci. NRC Research Press Ottawa, Canada; 1989; 46: 670±680. doi: 10.1139489-086; Robinson C L K, Ware D M, Parsons T R. Simulated annual plankton production in the northeastern Pacific Coastal Upwelling Domain. J Plankton Res. 1993; 15: 161±183. doi: 10.1093/plankt/15.2.161; Wijesekera H W, Gregg M C. Surface layer response to weak winds, westerly bursts, and rain squalls in the western Pacific Warm Pool. J Geophys Res. 1996; 101: 977±997; and Kara A B, Rochford P A, Hurlburt H E. An optimal definition for ocean mixed layer depth. J Geophys Res. 2000; 105: 16803. doi: 10.1029/2000JC900072, each incorporated herein by reference in their entirety. MLD and its variability has been well documented globally and regionally and has strong impact on near-surface acoustic applications, ocean biology and evolution of surface parameters like SST. See Kara A B, Rochford P A, Hurlburt H E. Mixed layer depth variability over the global ocean. J Geophys Res. 2003; 108: 1±15. doi: 10.1029/2000JC000736; de Boyer MonteÂgut C, Madec G, Fischer A S, Lazar A, Iudicone D. Mixed layer depth over the global ocean: An examination of profile data and a profile-based climatology. J Geophys Res Ocean. 2004; 109: 1±20. doi: 10.1029/2004JC002378; Lorbacher K, Dommenget D, Niiler P P, KoÈ hl a. Ocean mixed layer depth: A subsurface proxy of ocean-atmosphere variability. J Geophys Res. 2006; 111: C07010. doi: 10.1029/2003JC002157; Thomson R E, Fine I V., Columbia B, Columbia B. Estimating mixed layer depth from oceanic profile data. J Atmos Ocean Technol. 2003; 20: 319±329. doi: 10.1175/1520-0426 (2003)020<0319:EMLDFO>2.0.CO;2; Zeng L, Du Y, Xie S-P, Wang D. Barrier layer in the South China Sea during summer 2000. Dyn Atmos Ocean. 2000; 47: 38±54; Zeng L, Wang D. Seasonal variations in the barrier layer in the South China Sea: characteristics, mechanisms and impact of warming. Clim Dyn. Springer Berlin Heidelberg; 2016; 1±20. doi: 10.1007/s00382-016-3182-8; D'Ortenzio F, ludicone D, de Boyer Montegut C, Testor P, Antoine D, Marullo S, et al. Seasonal variability of the mixed layer depth in the Mediterranean Sea as derived from in situ profiles. Geophys Res Lett. 2005; 32: 1±4. doi: 10.1029/2005GL022463; Houpert L, Testor P, Madron X D De, Somot S, Ortenzio F D. Seasonal cycle of the mixed layer depth, of the seasonal thermocline and of the upper-ocean heat rate in the Mediterranean Sea derived from observations. Geophys Res Abstr. Elsevier Ltd; 2014; 16: 15100. doi: 10.1016/j.p-ocean.2014.11.004; Sutton P J, Worcester P F, Masters G, Cornuelle B D, Lynch J F. Ocean mixed layers and acoustic pulse propagation in the. J Acoust Soc Am. 2014; 94: 1517±1526. doi: 10.1121/1.408130; Polovina J, Mitchum G T, Evans T. Decadal and basin-scale variation in mixed layer depth and the impact on biological production in the Central and North Pacific, 1960±88. Deep Sea Res. 1995; 42:1701±1716; and Alexander M, Scott J, Deser C. Processes that influence sea surface temperature and ocean mixed layer depth variability in a coupled model. J Geophys Res Ocean. 2000; 105: 16823±16842. doi: 10.1029/2000jc900074, each incorporated herein by reference in their entirety.

DESCRIPTION OF THE RELATED ART

Previous studies adopted different approaches to identify MLD. The simplest approach is the threshold method which is widely used both regionally and globally. See Lim S, Jang C J, Oh I S, Park J. Climatology of the mixed layer depth in the East/Japan Sea. J Mar Syst. Elsevier B. V.; 2012; 96±97: 1±14. doi: 10.1016/j.jmarsys.2012.01.003, incorporated herein by reference in its entirety. Another common approach is gradient method that also is used in small and large scale studies. See Brainerd K E, Gregg M C. Surface mixed and mixing layer depths. Deep Sea Res Part I Oceanogr Res Pap. 1995; 42: 1521±1543. doi: 10.1016/0967-0637(95)00068-H; Dong S, Sprintall J, Gille S T, Talley L. Southern Ocean mixed-layer depth from Argo float profiles. J Geophys Res. 2008; 113: 1±12. doi: 10.1029/2006JC004051; and Holte J, Talley L. A New Algorithm for Finding Mixed Layer Depths with Applications to Argo Data and Subantarctic Mode Water Formation *. J Atmos Ocean Technol. 2008; 26: 1920±1939. doi: 10.1175/2009JTECHO543.1, each incorporated herein by reference in their entirety. Recently Lorbacher et al. estimated MLD using curvature of the profile. Threshold and gradient methods fix MLD at the shallowest depth where chosen threshold or gradient is achieved. Curvature method searches for the first extreme curvature of the profile, analyzes the profile at nearby levels and defines MLD. Lorbacher et al. visually examined 500 random profiles from various parts of the world and found that estimates from curvature method are better than threshold method for 63% of profiles and vice versa for 10% while for the remaining 27% it is not clear which method is reproducing the adequate MLD.

Gulf of Aden (GA), a marginal sea that connects the Red Sea with the Indian Ocean, augments east-northeastward from the narrow Strait of Bab-el-Mandab to a line interfacing Ras Baghashwa (east of Mukalla, Yemen) and Ras-Asir (northern corner of the Somali Peninsula). It is 900 km long and spreads over an area of around 220×103 km$^2$ with an average depth of 1800 m, and is strongly influenced by seasonally reversing winds. Circulation and hydrographic changes are largely forced by seasonal changes in wind pattern. See Al-Saafani M A. Physical Oceanography of the Gulf of Aden. PhD thesis, Goa Univ. 2008; and Al-Saafani M A, Shenoi S S C. Water Masses in the Gulf of Aden. J Oceanogr. 2007; 63: 1±14. doi: 10. 1007/s10872-007-0001-1, each incorporated herein by reference in their entirety.

Compared to other regions of the world, information of MLD and its variability is sparse in the Gulf of Aden. MLDs detected using available conventional (e.g., threshold, gradient and curvature) methods are mismatching considerably with each other at the same and adjacent stations.

One objective of the present disclosure is to provide a method for MLD estimation, for example, for use in the Gulf of Aden and to thereby estimate, predict, identify and/or calculate seasonal variability.

To determine temperature and salinity profiles two hydrographic datasets were used. First is the NODC (National Oceanographic Data Center, http://www.nodc.noaa.gov/005/SELECT/dbsearch/dbsearch.html) product of temperature and salinity measured using CTD/STD (conductivity-temperature-depth/salinity-temperature-depth) and second is the REDSOX (Red Sea Outflow Experiment) cruise profiles. About 433 CTD profiles are available in the Gulf of Aden region from NODC, out of it 132 belong to winter (December-March) and 217 belong to summer (June-September) while the remaining belong to inter-seasons. REDSOX experiment provided 238 profiles during winter (February-March) and 227 during summer (August-September) in the year 2001. See Peters H, Johns W E. Mixing and Entrainment in the Red Sea Outflow Plume. Part II: Turbulence Characteristics. J Phys Oceanogr. 2005; 35: 584±600. doi: 10.1175/JPO2689.1; and Johns W, Peters H, Zantopp R, Bower A, Fratantoni D. CTD/O2 measurements collected aboard the RN Knorr, February±March 2001: REDSOX-1. Tech Rep. 2001; 54: University of Miami, each incorporated herein by reference in their entirety. CTD profiles from REDSOX experiment are used to compare MILD identification methods. Seasonal MLD structure was analyzed using all available CTD profiles described herein.

Additionally, satellite altimetry data (Sea Level Anomalies, SLA) from AVISO (ftp://ftp.aviso.altimetry.fr/global/delayed-time/grids/msla/all-sat-merged/h/) were used to understand sea level changes of the region. Satellite estimates of TOPEX/Poseidon, Jason-1, ERS-1/2, and Envisat were merged together to produce SLA which is available on 0.25×0.25 degree grid from 1992 to present. Detailed information on SLA product and data processing are well documented. See Ducet N, Le Traon P Y, Reverdin G. Global high-resolution mapping of ocean circulation from TOPEX/Poseidon and ERS-1 and -2. J Geophys Res. 2000; 105: 19477. doi: 10.1029/2000JC900063; and Le Traon P Y, Dibarboure G. Mesoscale mapping capabilities of multiple-satellite altimeter missions. J Atmos Ocean Technol. 1999; 16: 1208±1223. doi: 10.1175/1520-0426(1999)016<1208: MMCOMS>2.0.CO;2, each incorporated herein by reference in their entirety. SLA in the year 2001 was analyzed to see the effect of sea level changes on mixed layer structure.

A comparison of results from conventional methods with a segment method is described herein. A short description of each conventional method is presented below.

Threshold, gradient, and curvature methods were applied to identify MLD in the Gulf of Aden. Researchers used different threshold values for both temperature and potential density (here density is used instead of potential density). The most common value is 0.2° C. for temperature and 0.03 kgm$^{-3}$ for density. Various thresholds were used from 0.1° C. to 1.0° C. for temperature and from 0.01 to 0.10 kgm$^{-3}$ for density. Dong et al. reported a suitable value of temperature gradient as 0.025° C. m$^{-1}$. Holte et al. used temperature gradient as 0.005° C. m$^{-1}$ and potential density gradient as 0.0005 kg m$^{-3}$ db$^{-1}$ for Antarctic and sub-Antarctic profiles. Brainerd et al. used different potential density gradient values ranging from 0.0005 to 0.05 kg m$^{-3}$ m$^{-1}$. Gradients from 0.005 to 0.05° C. m$^{-1}$ were used for temperature and from 0.0005 to 0.03 kg m$^{-3}$ m$^{-1}$ for density. The curvature method identifies MLD with the help of gradient and curvature of profile. MLD is the first maximum of curvature in temperature or density profile with significant gradient at deeper levels.

Different methods show significantly different MLD values for the same profile. Similarly substantial differences are observed in MLD of adjacent stations with the same method. Close evaluation of individual profiles revealed ineffectiveness of conventional methods for a large number of profiles. In the case of profiles where conventional methods detected nearly accurate MLD, curvature method showed better agreement. Lorbacher et al. found that curvature method is better than threshold method for most parts of global ocean.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to embodiments of the disclosed subject matter, a method for determining a mixed layer depth (MLD) in a body of water includes receiving a vertical high resolution profile corresponding to the body of water. Additionally, a profile segment corresponding to a portion of the profile between a surface of the body of water and a bottom of a thermocline is selected to be analyzed. Further, a depth within the profile segment corresponding to MLD is identified. For example, the mixed layer depth (MLD) in the Gulf of Aden is analyzed using vertical high resolution (1 m) profiles of both temperature and density. Firstly, threshold and gradient methods were examined for estimating the MLD. Close evaluation with individual profiles reveals the failure of both methods for most of the profiles. Furthermore, the curvature method, a relatively recent approach to define ocean MLDs, is established for open water profiles, but for marginal seas, like the Gulf of Aden, it detects shallower depths than the actual MLD. The present disclosure describes a segment method that resolves these significant differences. The segment method approach includes a partial curvature method. The segment method produces MLD estimates for more than 95% of the profiles and overcomes major limitations of conventional methods. The segment method is less biased and least scattered compared to other methods with a correlation coefficient>0.95. Using the segment method it was determined that the mixed layer in Gulf of Aden displays significant seasonal variability and is deeper in winter. Throughout the year, the western part of gulf experiences deeper mixed layer than the eastern part. Regional eddies dominate Gulf of Aden's MLD pattern during all seasons.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A illustrates a temperature based threshold mixed layer depth (MLD) profile during winter according to one or more aspects of the disclosed subject matter;

FIG. 2B illustrates a temperature based threshold MLD profile during summer according to one or more aspects of the disclosed subject matter;

FIG. 2C illustrates a temperature based gradient MLD profile during winter according to one or more aspects of the disclosed subject matter;

FIG. 2D illustrates a temperature based gradient MLD profile during summer according to one or more aspects of the disclosed subject matter;

FIG. 2E illustrates a temperature based curvature MLD profile during winter according to one or more aspects of the disclosed subject matter;

FIG. 2F illustrates a temperature based curvature MLD profile during summer according to one or more aspects of the disclosed subject matter;

FIG. 3A illustrates an exemplary winter profile according to one or more aspects of the disclosed subject matter;

FIG. 3B illustrates an exemplary summer profile according to one or more aspects of the disclosed subject matter;

FIG. 3C illustrates an exemplary winter profile according to one or more aspects of the disclosed subject matter;

FIG. 3D illustrates an exemplary summer profile according to one or more aspects of the disclosed subject matter;

FIG. 4A illustrates the difference between conventional and segment method based on a threshold MLD profile during winter according to one or more aspects of the disclosed subject matter;

FIG. 4B illustrates the difference between conventional and segment method based on a threshold MLD profile during summer according to one or more aspects of the disclosed subject matter;

FIG. 4C illustrates the difference between conventional and segment method based on a gradient MLD profile during winter according to one or more aspects of the disclosed subject matter;

FIG. 4D illustrates the difference between conventional and segment method based on a gradient MLD profile during summer according to one or more aspects of the disclosed subject matter;

FIG. 4E illustrates the difference between conventional and segment method based on a curvature MLD profile during winter according to one or more aspects of the disclosed subject matter;

FIG. 4F illustrates the difference between conventional and segment method based on a curvature MLD profile during summer according to one or more aspects of the disclosed subject matter;

DETAILED DESCRIPTION

Figure 1:
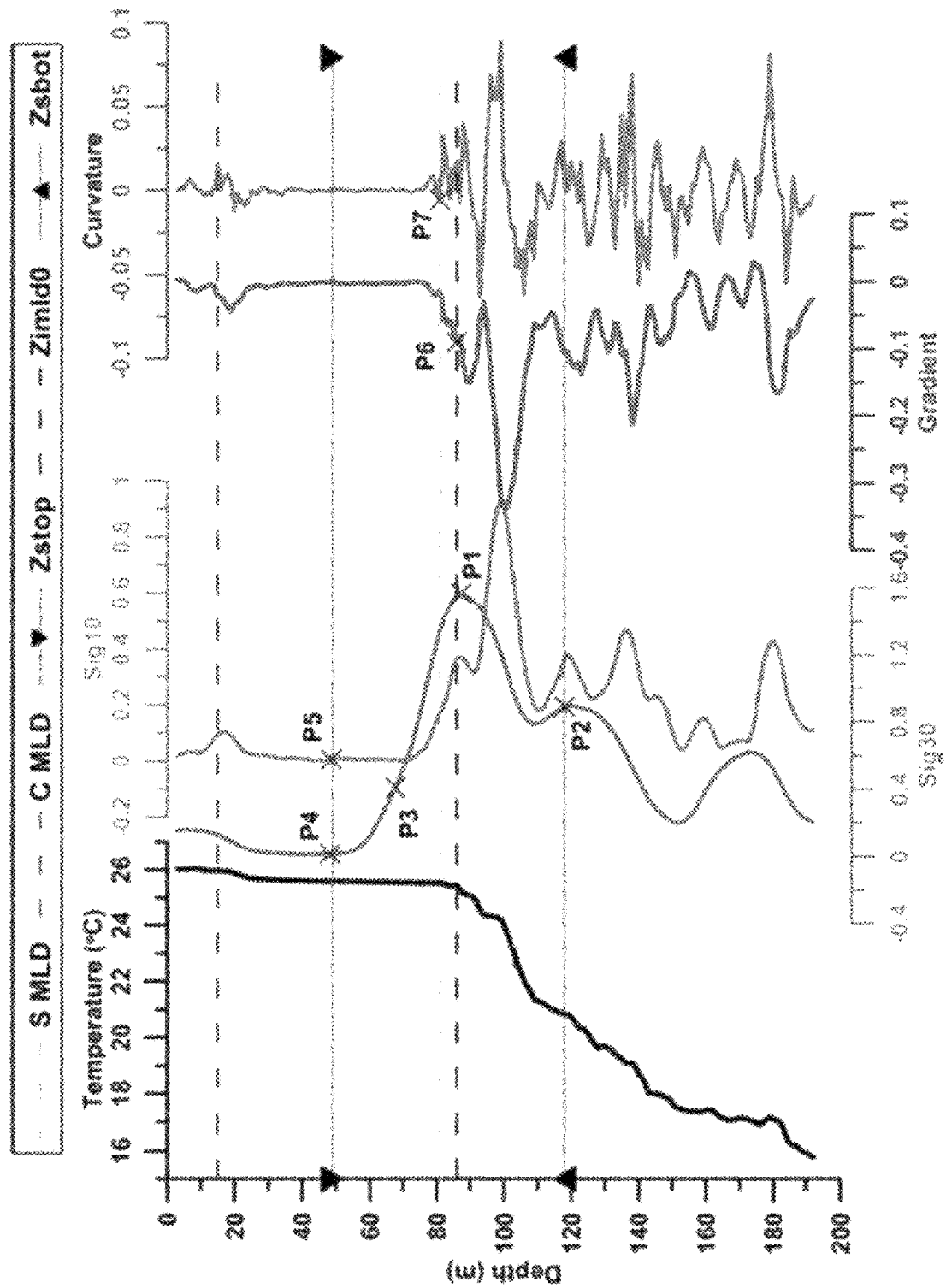
FIG. 1 illustrates a typical temperature profile to show the procedure of segment method according to one or more aspects of the disclosed subject matter.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

Referring now to the drawings, wherein like reference numerals designate identical or corresponding parts throughout the several views.

FIG. 1 illustrates a typical temperature profile to show the procedure of segment method according to one or more aspects of the disclosed subject matter. In FIG. 1, sig30 (standard deviation for every lower 30 m water column), sig10 (standard deviation for every lower 10 m water column), gradient (with respect to lower 5 m interval) and curvature of temperature are plotted in green, skyblue, red, and blue colors, respectively. Horizontal lines with upward and downward pointed triangle marks top and bottom ends of profile segment, respectively. Dashed lines represent MLD by curvature method (red), MLD by segment method (green), and first guess MLD (black). Depths marked as P1, P2, P3, P4, P5, P6, and P7 are described further herein.

The profile can be analyzed from $Z_{stop}$ to bottom ($Z_{sbot}$) to find the closest level to MLD, wherein $Z_{stop}$ is a top of the profile segment and $Z_{sbot}$ is a bottom of the profile segment as shown in FIG. 1. At first, the shallowest depth where $|g_T(i)|>0.25*\max|g_T|$ and $\sigma 30(i)>0.02$ can be identified (represented as $Z_{imld0}$ and denoted by P6 in FIG. 1), wherein $g_T(i)$ is the gradient at a predetermined interval (i) and $\sigma_{30}(i)$ is the standard deviation of temperature in a 30 meter interval below a current depth. The second criterion can make sure that estimated MLD is at a location with significantly inhomogeneous deeper levels. Usually, $Z_{imld0}$ can be found at a shallower end of the thermocline and below MLD.

Standard deviation of $g_T$ at interval $[Z_{stop}, Z_{imld0}]$, (denoted as G0 denotes range of variability in the interval. Following Lorbacher et al., closest level to MLD ($Z_{imid}$, also denoted by P7 in FIG. 1) is the shallowest depth where minima/maxima of the curvature falls together with positive/negative gradient $g_T$. In addition, two conditions can also be applied to confirm MLD. First, $|g_T|>\sigma_{gt}$ can assure a threshold for significant local inhomogeneity in the profile. Second, $\sigma_{30}(i)>0.02$ can confirm that the level identified is above the region of rapid changes. For low resolution profiles, it is preferred to apply interpolation to get more precise MLD. Interpolation process applied in Lorbacher et al. may also be used. If no extreme value is found in the profile segment, then the first level where $|g_T| \geq 0.7*\max|g_T|$ is considered as MLD. Such MLDs are flagged. None of the profiles of both winter and summer season faced this situation. A flowchart showing the steps of MLD estimation procedure can be seen in FIG. 10.

FIGS. 2A-2F illustrates a temperature based mixed layer depth (MLD) profile during winter (FIG. 2A, FIG. 2C, and FIG. 2E) and summer (FIG. 2B, FIG. 2D, and FIG. 2F), wherein FIGS. 2A and 2B correspond to a conventional threshold profile MLD profile, FIGS. 2C and 2D correspond to a conventional gradient MLD profile, and FIGS. 2E and 2F correspond to a conventional curvature MLD profile according to one or more aspects of the disclosed subject matter.

Conventional methods are used to identify MLD of the region in both winter and summer using temperature and density profiles from REDSOX experiment. FIGS. 2A-2F show the estimated MLD using threshold (e.g., with common threshold criteria for temperature, 0.2° C.), gradient (e.g., with common gradient criteria 0.025° C.), and curvature methods.

Estimated mean MLD using common temperature threshold (FIGS. 2A and 2B) during winter and summer can be respectively 35 m and 15 m, with minimum 11 m and maximum 102 m in winter and minimum 10 m and maximum 39 m in summer, for example. Temperature and density profiles can be used in the analysis, and the results for both are similar. Hereafter, if not specified, statistical parameters like mean, maximum, bias, correlation coefficient, etc. are explained based on temperature profile only. FIGS. 2C and 2D shows estimated MLD in the region using the gradient method with a gradient of 0.025° C., for example. Obtained mean MLD with gradient approach is 65 m in winter and 22 m in summer, with minimum 29 m and maximum 116 m in winter and a minimum 10 m and maximum 50 m in summer. MLD based on curvature method (FIGS. 2E and 2F) show mean MLD as 47 m in winter and 20 m in summer, with the minimum at 12 m and maximum at 111 m in winter and minimum 10 meters and maximum 47 m in summer. MLD values based on threshold, gradient, and curvature methods differ from each other at many locations.

FIG. 3A-3D illustrates profiles marked with MLD based on different methods for four sample stations (e.g., FIGS. 3A-3D). FIGS. 3A and 3C are winter profiles and FIGS. 3B and 3D are summer profiles. Threshold (Gradient) MLDs are marked on green (orange) vertical line. Curvature (segment) method based MLD is marked by horizontal line with a dot in blue (red) color. Letters $^a$Th$^o$ and $^a$Gr$^o$ are used in labels to represent threshold and gradient methods. Numbers in the tail of label indicate used threshold (0.1, 0.2, 0.3, 0.4, 0.5, 0.6, 0.7, 0.8, 0.9, and 1.0 respectively) and gradient (0.005, 0.01, 0.015, 0.02, 0.025, 0.03, 0.035, 0.04, 0.045, and 0.05 respectively).

Above approaches from FIGS. 2A-2F show considerable differences in estimated MLD in both winter and summer. Close observation of individual profiles and corresponding MLD values revealed the limitations of each method. Temperature based estimates of MLD using threshold, gradient, curvature and segment based approaches for four sample stations are shown in FIGS. 3A-3D. FIG. 3A FIG. 3C are during winter and FIG. 3B and FIG. 3D are during summer.

MLD for FIG. 3A, using threshold approach can be between 50 to 70 m, and with gradient method is around 45 m, for example. Additionally, both curvature and segment methods detect MLD at 48 m. MLD observed at FIG. 3B with all threshold and gradient criterions can be between 20 to 30 m while curvature and segment methods detect at the same depth.

In the case of the profile in FIG. 3C, lower criterions for threshold method and gradient method can define MLD between approximately 20 to 30 m while at 90 m for the remaining, for example. Curvature method can be defined at 15 m and segment method can be defined at 81 m. Segment method based MLD can be nearly five times greater compared to curvature based MLD. For profiles in FIG. 3D, the threshold method can detect between 10 m to 55 m while almost all of the gradient criterion detect MLD to be approximately 11 m, for example. Curvature method can define MLD at 11 m for a predetermined temperature, whereas segment method can define MLD at approximately 55 m. Considering profiles at FIG. 3A and FIG. 3B, it should be appreciated that most of the criterion detect MLD at nearby (<5 m difference) levels, which can imply these are applicable for profiles having nearly ideal structure. But in the case of profiles in FIG. 3C and FIG. 3D, detected MLD by different methods has a substantial difference from one another. For some profiles, such differences are many times larger than the other.

FIG. 4A-4D illustrates the difference between conventional and segment method based MLD estimates for profiles during winter (FIGS. 4A, 4C, and 4E) and summer (FIGS. 4B, 4D, and 4F). Threshold, gradient and curvature maps are shown in FIGS. 4A-4B, FIGS. 4C-4D, and FIGS. 4E-4F, respectively.

The differences in estimated MLD between conventional methods and segment method can be seen in FIGS. 4A-4F. The difference between MLDs shows spatio-temporal variability at most of the stations. The number of stations having higher difference is more in winter than in summer. Most of the stations at the western part of gulf experienced large differences. MLD estimates based on curvature method show small differences at a relatively large number of stations, especially during summer. Generally, higher extreme criterions showed overestimation while lower extremes resulted in underestimation (e.g., see FIGS. 3A-3D).

To analyze the performance of MLD estimation, Lorbacher et al. selected 500 profiles from various parts of the world and manually compared their method to threshold method. Similarly, the best MLD from four methods (threshold, gradient, curvature, and segment), are compared with a visually defined MLD (fixed by manual observation of each profile, hereafter VMLD). VMLD is the bottom of visibly quasi-homogeneous upper layer with a rapidly varying lower water column. Quality index (as described in FIGS. 5A-5B) can be used to confirm the reliability and accuracy of VMLD.

A number of stations available in each grid can have a significant spatial difference with a relatively higher number of stations in the western part of the area being analyzed (e.g., see FIGS. 2A-2F). Statistical analysis for all profiles may represent the region with the higher number of profiles (e.g., west GA). Keeping this in mind, randomly selecting one profile for every 0.25° *0.25° bin can be used for comparison.

Figures 5A, 5B:
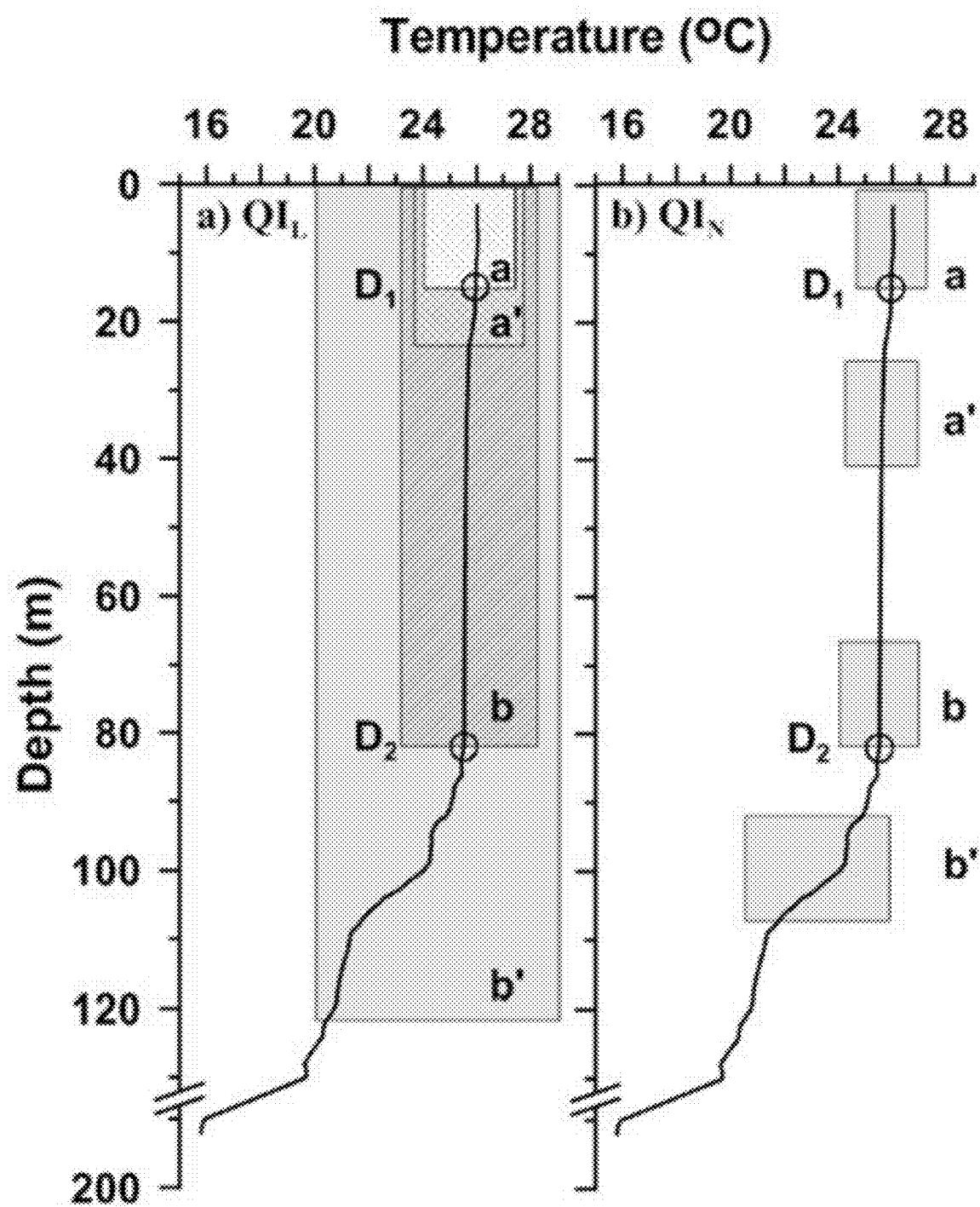
FIG. 5A illustrates a schematic diagram of a quality index using $QI_L$ according to one or more aspects of the disclosed subject matter.
FIG. 5B illustrates a schematic diagram of a quality index using $QI_N$ according to one or more aspects of the disclosed subject matter.

FIG. 5A-5B illustrates a schematic diagram of a quality index using $QI_L$ (quality index) and $QI_N$ according to one or more aspects of the disclosed subject matter. Additionally, D1 and D2 are two arbitrary depths to check performance of QI. Shaded boxes are labeled as a & a' and b & b', representing the portion of profile used to calculate standard deviation at D1 and D2, respectively.

A quality index can be prepared based on the notion that MLD is the bottom of nearly-homogeneous surface layer followed by a rapidly varying lower layer. Standard deviation of the variable from surface to MILD is expected to be nearly zero and that of deeper levels substantially high. Quality index can be estimated at arbitrary depths D1 and D2 (FIG. 5A) as:

$$QI_L = 1 - \frac{c}{c'} = 1 - \frac{\sigma(T_i - T_{mean}) \mid (z1, MLD)}{\sigma(T_i - T_{mean}) \mid (z1, 1.5*MLD)} \quad (1)$$

where σ denotes standard deviation with respect to vertical mean from nearest surface depth (z1) to MLD or 1.5*MLD. Letters c & c' (portion of the profile used to calculate σ) represented by a & a' at D1 and b & b' at D2. Based on $QI_L$, quality of MLD is categorized into three: 1—"well-defined" ($QI_L$>0.8), 2—"uncertainty present" ($QI_L$ between 0.5 and 0.8) and 3—"no direct interpretation possible" ($QI_L$<0.5).

$QI_L$ has been applied on profiles to get the accuracy of MLD estimation. It has been found that $QI_L$ satisfactorily estimates the quality of MLD for most of the profiles. In some cases where the profiles have short range gradient within the mixed layer, $QI_L$ is found to have higher value for bad MLD estimates also. To overcome this limitation a (additional) quality index is introduced. The additional quality index ($QI_N$) is defined at arbitrary depths D1 and D2 (FIG. 5B) as:

$$QI_N = 1 - \frac{c}{c'} = 1 - \frac{\sigma(T_i - T_{mean}) \mid (MLD - 15m, MLD)}{\sigma(T_i - T_{mean}) \mid (MLD + 10m, MLD + 25m)}, \quad (2)$$

where a is calculated for 15 m water column just above (b) and 10 m below (b') of MLD as shown in FIG. 5B. A 10 m gap is kept between b and b' to keep away the short range gradient (if any present) from calculation. FIGS. 5A and 5B show schematic diagram of quality index calculation at two arbitrary depths, which were selected to compare the performance of quality index, a very shallow depth (e.g., $D_1$ at 15 m) and a more realistic depth where MLD is located (e.g., $D_2$ at 82 m).

The corresponding values of $QI_L$ and $QI_N$ at depth D1 are 0.7 and 0.21 while at depth D2 are 0.91 and 0.99. The values of $QI_L$ and $QI_N$ are high at depth D2, indicating good quality of MLD estimation. But at D1, $QI_L$ is relatively high (close to 0.8) and $QI_N$ is very small, where small values are expected. The high value of $QI_L$ is due to the presence of short range gradient at depth D1. Quality of MLD estimation is determined by considering both $QI_L$ and $QI_N$. $QI_N$≤0.8 indicates the presence of inhomogeneity in the upper layer. If both $QI_L$ and $QI_N$ are ≥0.8, then defined MLD can be assumed to be "well-defined". The values of quality index and corresponding quality category are tabulated as shown in Table 1.

Out of the VMLD defined profiles, 86% come under the well-defined category with $QI_L$≥0.8 and $QI_N$≥0.8, while the rest have $QI_L$≥0.7 and $QI_N$≥0.8. VMLDs that come under the well-defined category are only used for comparison, to guarantee higher accuracy and reliability on manually defined VMLD.

TABLE 1

Quality category and corresponding values of $QI_L$ and $QI_N$.

| | $QI_N$ | $QI_L$ | Quality category |
|---|---|---|---|
| 1 | ≥0.8 | ≥0.8 | Well defined |
| | | 0.5-0.8 | Acceptable MLD |
| | | <0.5 | No direct interpretation possible |
| 2 | 0.5-0.8 | ≥0.8 | Uncertainty present |
| | | <0.8 | No direct interpretation possible |
| 3 | <0.5 | Any | No direct interpretation possible | doi: 10.1371/journal.pone.0165136.t001

Figures 6A, 6B:
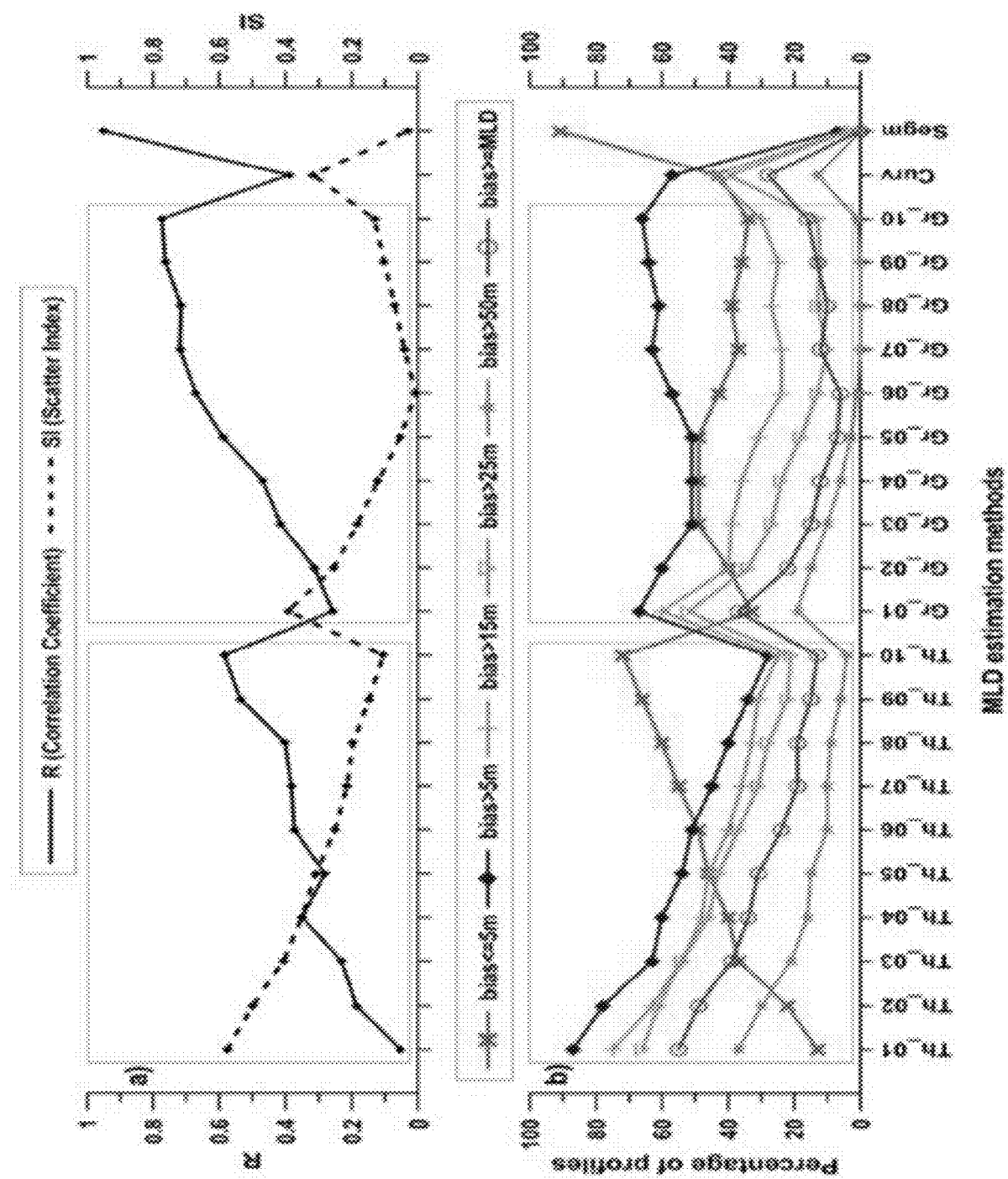
FIG. 6A is a graph illustrating the statistical parameters calculated for threshold, gradient, curvature and segment methods with respect to VMLD according to one or more aspects of the disclosed subject matter.
FIG. 6B is a graph illustrating bias according to one or more aspects of the disclosed subject matter.

FIG. 6A is a graph illustrating the statistical parameters calculated for threshold, gradient, curvature and segment methods with respect to VMLD according to one or more aspects of the disclosed subject matter, and FIG. 6B is a graph illustrating bias according to one or more aspects of the disclosed subject matter. Additionally, two boxes are drawn in both figures which can represent different threshold (left box) and gradient (right box) criterions, for example. R (correlation coefficient) and SI (Scatter index) are plotted in FIG. 6A, and bias is plotted in FIG. 6B. "Th" in the label represents threshold method and the number given at tail of each label denotes the respective criterion (similarly "Gr" for gradient method). "Cure" and "Segm" represent curvature and segment methods, respectively.

The difference between VMLD and method based MLD can be analyzed over the region. Since the mixed layer is thicker in winter than summer, difference between VMLD and method based MLD may be larger in winter than in summer. Accordingly, analyses corresponding to FIGS. 6A-6B can be based on winter profiles, for example. Summer profiles may also produce similar results, but can be weaker than those in winter.

Statistical parameters computed for threshold, gradient, curvature and segment based approaches against VMLD are shown in FIGS. 6A-6B. Temperature thresholds can vary from 0.1° C. to 1.0° C., for example. Common temperature threshold used in threshold method can be 0.2° C., for example, which showed weak correlation (e.g., see FIG. 6A). About 61% of profiles showed 25 m or more bias, and of those profiles, 30% have >50 m bias. For 49% of profiles, the detected MLD is just half or less than that of VMLD. Higher thresholds examined also failed to identify realistic MLD in many cases with overestimation. For a threshold of 1.0° C. (e.g., the highest of the selected thresholds and 5 times greater than commonly used 0.2° C.), approximately 25% and 21% of profiles show a bias of 15 m and 25 m, respectively. All of the thresholds are weakly correlated with VMLDs. Lower thresholds are well scattered (e.g., SI>0.5) and scattering gradually decreased to higher threshold end (e.g., SI<0.2). Observed bias is greater than the detected MLD itself for 50% of profiles at lower thresholds and close to 20% at higher thresholds.

Threshold method can be strongly dependent on chosen criterion. As threshold becomes larger, detected mixed layer becomes deeper (e.g., see FIG. 3D). In conditions where the vertical gradient is low, detected MLD for different thresholds can be significantly separated from each other. In the opposite case, the detected MLDs can be stickier (i.e., close to each other). For example, for a profile with low or weak gradient, the difference between the detected MLDs may be of the order of 10 to 15 meters. At the same time, for a profile with high or strong gradient, the difference between the detected MLDs may be of the order of 1 to 2 meters. Here in the low gradient case detected MLDs are significantly separated, while in the high gradient case the detected MLDs are very close to each other (i.e., stickier). Similarly, for two profiles with a similar mixed layer, the identified MLD can be different. Additionally, depending on the surface property value (e.g., SST), the identified MLD can be different. A profile with lower SST will show deeper MLD in such condition. Compared to segment method, threshold method has a poor estimation of MLD.

Gradient method has strong bias with respect to VMLD at lower gradients and becomes weaker at higher gradients. Gradient 0.03° C., for example, is the least scattered among 10 examined gradients with a correlation of 0.66, even though at this gradient 24% of profiles have a minimum 15 m bias. For the commonly used gradient (0.025° C.), 31% have a 15 m difference with low correlation (0.58). Gradients≥0.03° C. are relatively better correlated to VMLD estimates, but nearly 30% of profiles show at least 15 m bias for all gradient thresholds. The analysis shows gradient method is better than threshold method, but still has considerable weaknesses.

Similar to threshold method, gradient method also shows strong dependence on chosen gradient criterion. Further, in regions with small intrusion or short scale gradient in the profiles, gradient method can detect MLD at such depths in most cases, which leads to large differences between detected and actual mixed layer, thereby strongly indicating the ineffectiveness of gradient method for GA region.

In curvature method, 40% of profiles show a bias of 25 m or higher while about 13% show 50 m bias. For nearly 28% of profiles, the detected MLD is just half of or lesser than that of VMLD. Curvature method is weakly correlated (e.g., 0.38) to VMLD estimates. Dynamically active regions may possess short range gradients within the mixed layer itself. In such circumstances, curvature method identifies MLD at short gradient depths, which often leads to early detection of MLD.

MLD estimates based on segment method have strong correlation (e.g., R=0.95) and least scattering (e.g., SI=0.02). Gradient criterion 0.03° C. also has similar value for SI but shows significant bias. In the case of segment method, among the whole used profiles only 4% has a bias of 15 m or more. Detected bias for 91% of profiles is 5 m or less. Out of the 22 methods used (10 based on threshold, 10 based on gradient, 1 based on curvature and 1 based on segment), the segment method is the least biased, least scattered and best correlated.

Segment method detects MLD at realistic depth and can avoid short range gradients or small scale intrusions, which are present in many profiles. Similar to curvature method, segment method can be free from dependence on property value at the reference depth, and it can be easily implemented to any region. For methods like threshold and gradient, it can be necessary to change chosen criterion with characteristics of the region. As an advantage to segment approach, segment approach does not have a requirement to change chosen criterion with characteristics of the region. Additionally, segment approach has the ability to overcome short range gradients and/or small scale intrusions.

In the case of profiles having ideal structures with no significant small scale gradients within the mixed layer, all the methods identify nearly equal MLDs (e.g., see FIG. 3B). Many profiles in GA have short range gradient at near surface depth with uniform characteristic layer beneath and followed by a clearly visible thermocline. For this reason, segment based approach can be used for MLD estimation in GA.

Figure 7B:
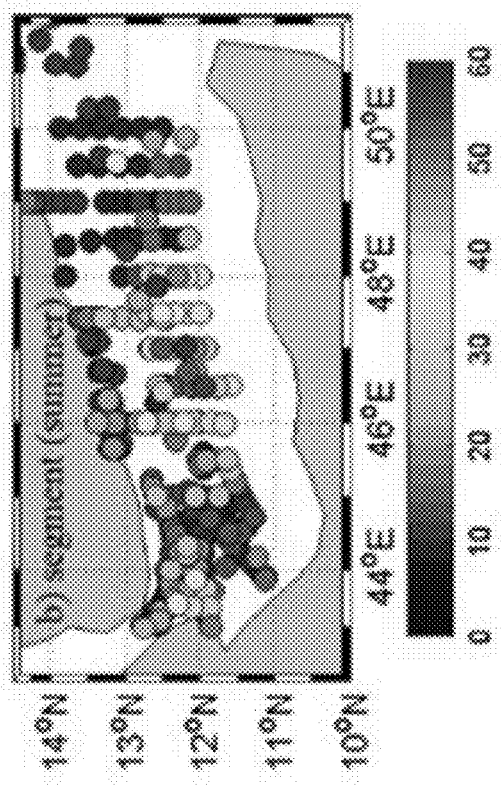
FIG. 7B is a map of MLD identified using temperature based on segment method for available CTD profiles during summer according to one or more aspects of the disclosed subject matter.
Figure 7A:
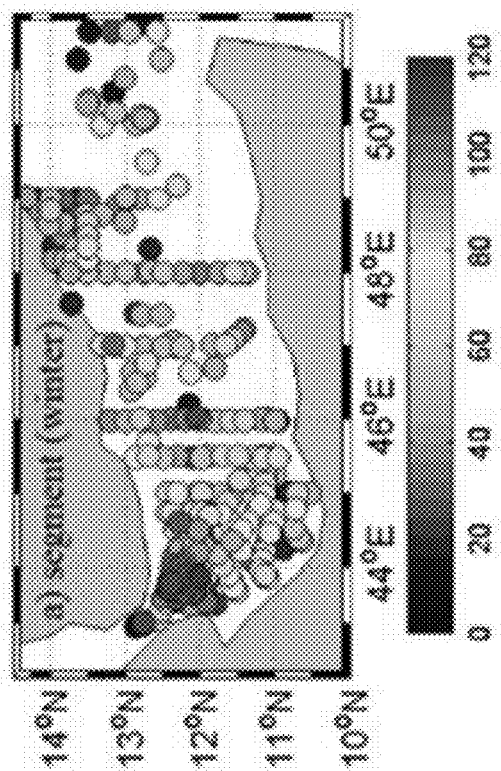
FIG. 7A is a map of MLD identified using temperature based on segment method for available CTD profiles during winter according to one or more aspects of the disclosed subject matter.

FIG. 7A is a map of MLD identified using temperature based on segment method for available CTD profiles during winter according to one or more aspects of the disclosed subject matter. FIG. 7B is a map of MLD identified using temperature based on segment method for available CTD profiles during summer according to one or more aspects of the disclosed subject matter. Segment method can be used to define MLD in the region using all available temperature profiles from CTDs during winter (e.g., December-March) and summer (e.g., June-September) months, as shown in FIGS. 7A-7B. Maximum MLD over the region during winter is 120 m at far west and the minimum is 22 m at far east with mean 77 m. Maximum MLD over the region during summer is 60 m at central part and the minimum is 10 m at west and east with mean 21 m.

Figure 8:
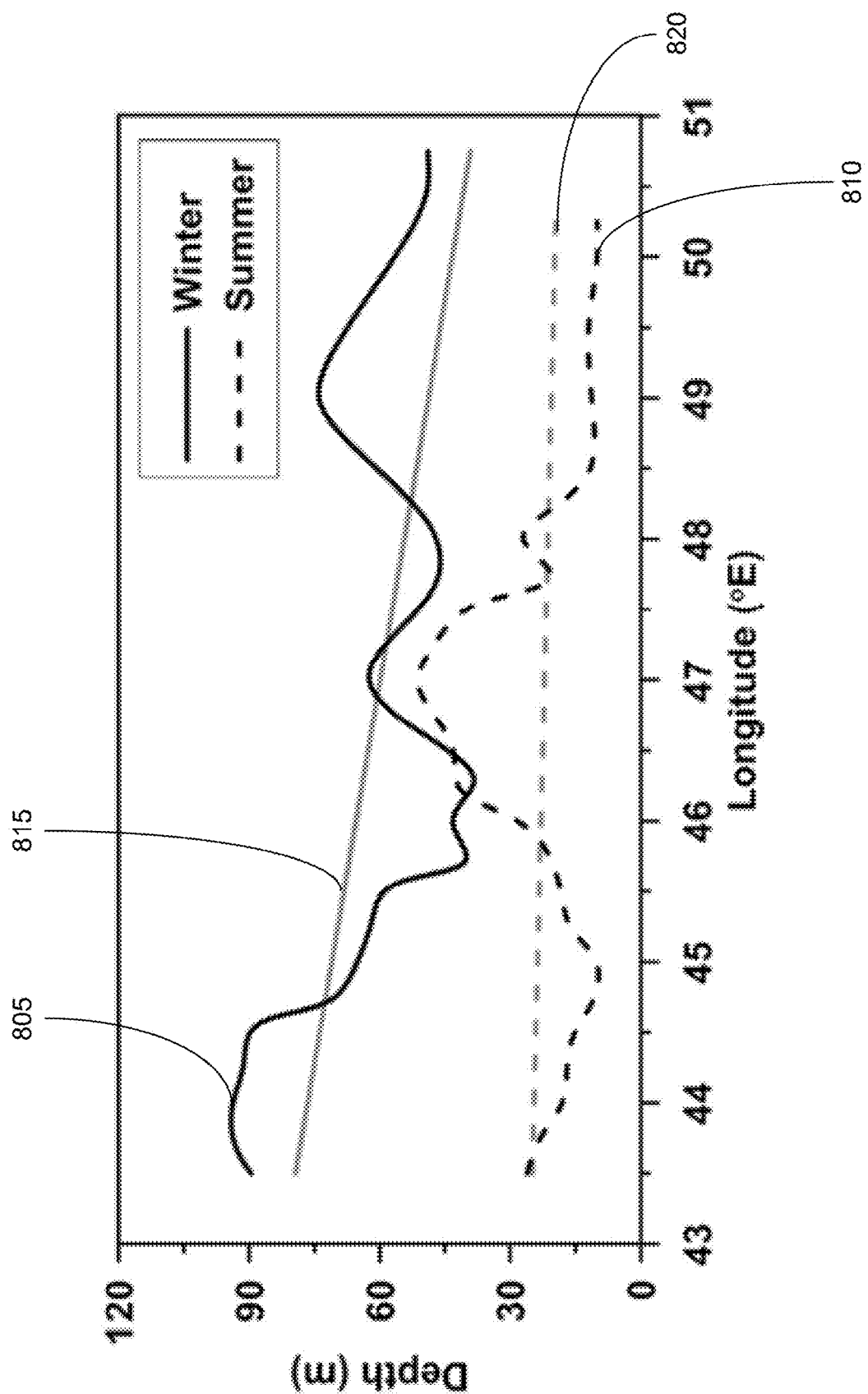
FIG. 8 is a graph illustrating MLD along the central axis of gulf extending from west to east for winter and summer according to one or more aspects of the disclosed subject matter.

FIG. 8 is a graph illustrating MLD along the central axis of gulf extending from west to east for winter and summer according to one or more aspects of the disclosed subject matter. Line 805 can represent MLD during winter, and line 810 can represent MLD during summer. Line 815 and line 820 can represent linear fit to winter and summer MLD, respectively.

Figures 9A, 9B:
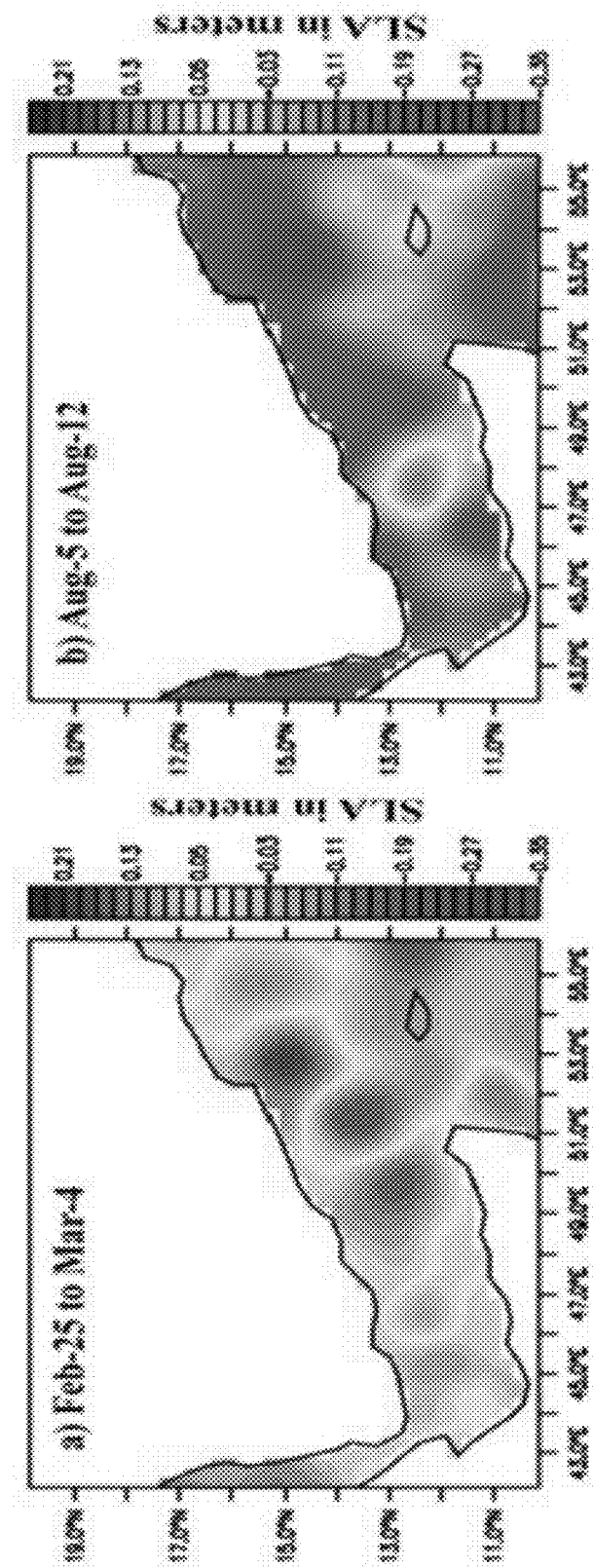
FIG. 9A illustrates SLA (in meters) from AVISO for a first date range according to one or more aspects of the disclosed subject matter.
FIG. 9B illustrates SLA (in meters) from AVISO for a second date range according to one or more aspects of the disclosed subject matter.

FIG. 9A illustrates SLA (in meters) from AVISO for a first date range according to one or more aspects of the disclosed subject matter. The first date range can correspond to 25 February to 4 March in 2001.

FIG. 9B illustrates SLA (in meters) from AVISO for a second date range according to one or more aspects of the disclosed subject matter. The second date range can correspond to 5 August to 12 August in 2001.

During winter, western GA has a deeper mixed layer and becomes shallower to the eastern side (e.g., see FIGS. 7A-7B and FIG. 8). Mean MLDs in western, central, and eastern parts of gulf can be 83 m, 57 m, and 49 m, respectively. Shallowing tendency of MLD towards east exists in summer also, but is weak (e.g., mean MLDs can be 20 m, 42 m and 17 m in west, central, and east, respectively). The mixed layer is shallow at western and eastern parts of the gulf with deeper mixed layer at a central part. Average MLD calculated along the axis of GA (e.g., along the straight line from 11.75N & 43E to 13.25N & 51.5E and meridionally averaged for +/−0.5 degrees) for winter and summer months of the year 2001 (the year with the largest number of observation) is shown in FIG. 8. MLD along the central axis can follow the general spatial pattern with higher values towards west and lower towards east.

GA experiences frequent cyclonic and anti-cyclonic eddies. Bower et al. found the presence of three eddies, two cyclonic and one anti-cyclonic using ADCP current measurements. See Bower A S, Fratantoni D M, Johns W E, Peters H. Gulf of Aden eddies and their impact on Red Sea Water. Geophys Res Lett. 2002; 29: 2025. doi: 10.1029/2002GL015342, incorporated herein by reference in its entirety. Sea Level Anomalies from AVISO are shown in FIGS. 9A-9B for two days respectively in winter and summer. Al-Saafani et al. confirmed the westward movement of eddies in the region. See Al-Saafani M a., Shenoi SSC, Shankar D, Aparna M, Kurian J, Durand F, et al. Westward movement of eddies into the Gulf of Aden from the Arabian Sea. J Geophys Res Ocean. 2007; 112: 1±12. doi: 10. 1029/2006JC004020, incorporated herein by reference in its entirety. Multiple numbers of eddies and movement towards the west can lead to complex dynamics in the region. During winter, south of the western GA has relatively shallower (e.g., 75 m) MLD than that of north (e.g., 110 m), which can be related to observed cyclonic eddy at south of the western part (e.g., FIG. 9A). Similarly, east of 48° E has deeper MLD than the surrounding region. Presence of the anti-cyclonic eddy centered at 49° E might have a deepening effect on MLD of the region. Cyclonic eddy at central part of the gulf also showed its signature in the MLD pattern with lower MLD values. In summer, MLD gradually becomes shallow from west to east, with abnormally deeper MLD at central part of the gulf (e.g., see FIG. 8). An anti-cyclonic eddy has existed at central gulf from June (figure not shown). This eddy intensified during July and continued until middle of August (e.g., see FIG. 9B), which might have significantly influenced mixing in the region and resulted in a deeper mixed layer.

Figure 10:
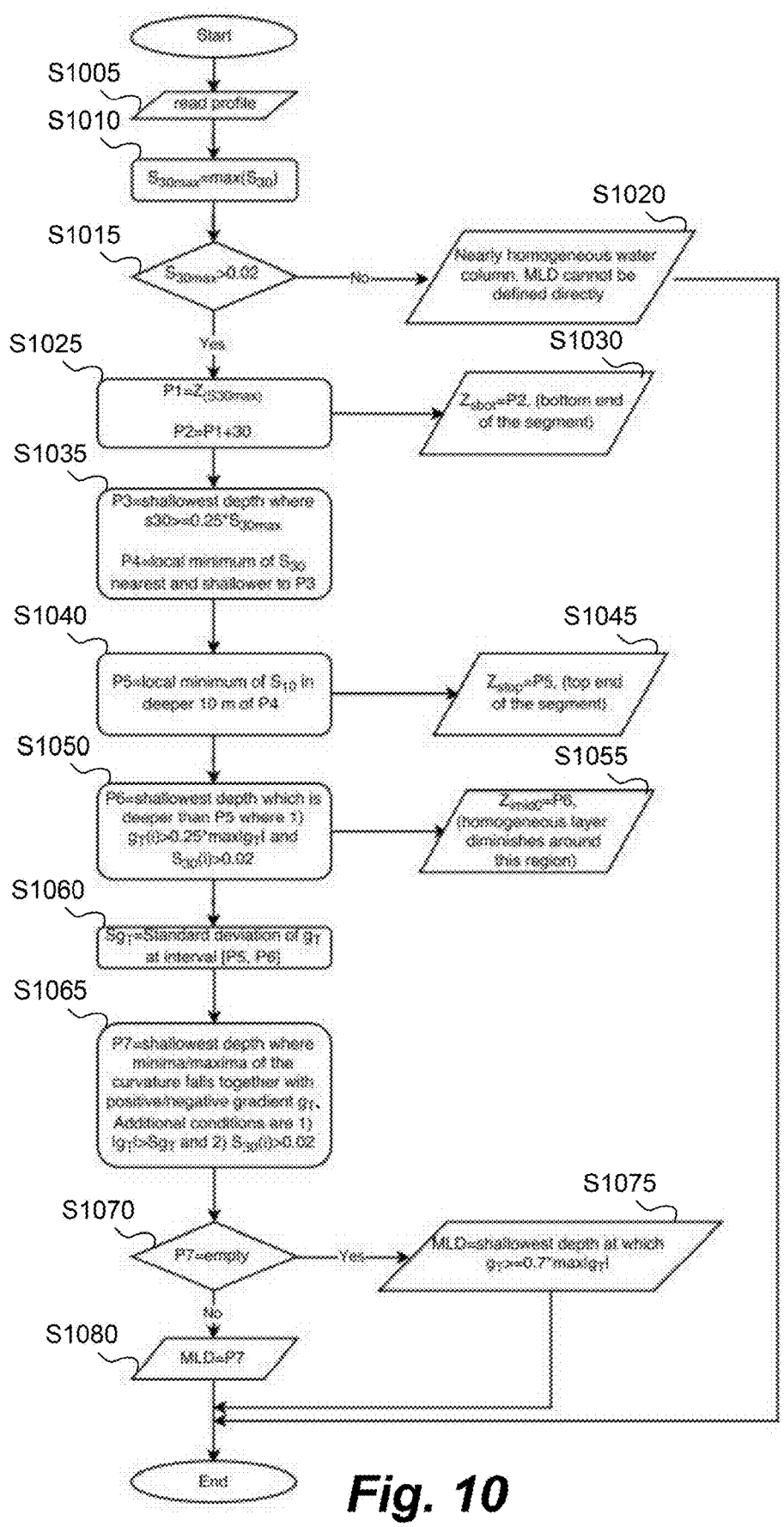
FIG. 10 is an algorithmic flow chart of a method for MLD estimation according to one or more aspects of the disclosed subject matter.

FIG. 10 is an algorithmic flow chart of a method for MLD estimation according to one or more aspects of the disclosed subject matter. The steps in FIG. 10 include P1, P2, P3, P4, P5, P6, and P7 with reference at least to FIG. 1, for example.

In S1005, a temperature profile can be read.

In S1010, the standard deviation of the profile for every 30 meters can be estimated for each level. The location of maximum $S_{30}$ can be denoted by $S_{30max}$.

In S1015, it can be determined if $S_{30max}$ is greater than 0.02. If $S_{30max}$ is less than 0.02, then it can be determined that a water column is at least a nearly homogeneous water column in S1020. As a result, the entire water column cannot be defined by MLD directly and the process can end. However, if $S_{30max}$ is greater than 0.02, then a water column can be determined to be inhomogeneous.

If $S_{30max}$ is determined to be greater than 0.02 in S1015, then the depth of $S_{30max}$ can be marked as P1 and the depth 30 m below P1 can be considered as P2 in S1025. P2 can be the bottom end of the segment, also denoted by $Z_{sbot}$, for example.

In S1035, the shallowest depth where $S_{30}>0.25*S_{30max}$ can be marked as P3. The local minimum of $S_{30}$ can be shallower and nearer to P3 and can be marked as P4.

In S1040, a local minimum within 10 meters deeper relative to P4 can be marked as P5. P5 can be a top end of a segment.

In S1045, $Z_{stop}$ can be equivalent to P5 which corresponds to the top end of the segment, for example.

In S1050, P6 can correspond to the shallowest depth which is deeper than P5 where gradient $g_T(i)>0.25*max|g_T|$ and $S_{30}(i)>0.02$. The homogeneous layer can diminish around this region.

In S1055, this depth can be denoted by P6 and $Z_{imld0}$, for example.

In S1060, the standard deviation of gradient ($S_{gT}$) in the interval from P5 to P6 can be estimated.

In S1065, MLD can be defined as the shallowest depth where minimum/maxima of the curvature fall together with positive/negative of gradient. Two additional conditions may also may need to be satisfied to fix the MLD. The conditions include $|g_T|>S_{gT}$ and $S_{30}(i)>0.02$. These conditions can ensure that the detected depth has significant variability and the deeper level is inhomogeneous. This depth can denoted by P7 or MLD, for example.

In S1070, it can be determined if P7 is not identified. If P7 cannot be identified, then in extreme cases where no such MLD locations can be identified, then the shallowest depth at which $g_T>0.7*max|g_T|$ can be considered as MLD in S1075. However, if P7 can be identified, then MLD can be equal to P7 in S1080.

As a result, MLD detected by conventional methods can analyzed in Gulf of Aden region. Threshold and gradient methods applied on temperature profiles with commonly used criterion (e.g., 0.03 kg m$^{-3}$ and 0.005 kg m$^{-3}$ m$^{-1}$) underestimate MLD by 20 m for ~50% of profiles in the analyzed area. Lower and higher extreme criterions used also failed to capture reliable depth of mixed layer with under or over estimation. For profiles with ideal shape, all techniques estimated MLD with an acceptable difference of <5 m. In such conditions, curvature method exhibited higher efficiency than threshold and gradient methods. For profiles with irregular shape, conventional methods are unable to identify realistic MLD due to the presence of short range gradients within the mixed layer itself. Segment method as described herein can perform MLD estimation which overcomes major limitations of conventional methods. Segment method has several advantages over threshold and gradient method including being independent of the property value at the surface like SST and estimated MLD is free from linear dependence on the used threshold or gradient criterion. In addition, segment method can overcome limitations of short-range gradient or small scale intrusion that may be present in highly dynamic regions. These advantages of segment method increase reliability and accuracy. Quality index definition used in this can be used to confirm the accuracy and reliability of estimated MLD.

Detected MLD by segment method can show temporal and spatial variability of mixed layer structure. In both winter and summer, the western part of gulf has deeper mixed layer and shallows gradually to the east (e.g., see FIGS. 7A-7B and FIG. 8). SLA of the region confirms the presence of cyclonic and anti-cyclonic eddies in the region. Eddies in the region influence water up to 1000 m and more and play significant role in mixed layer changes of the region. Deeper mixed layer at the central part of gulf during summer, against the general pattern, is due to the relatively strong anti-cyclonic eddy in the region during this period (FIG. 9B). Due to the complex nature of the region, detailed investigation on the influence of eddies and other parameters may formulate a clear picture of dynamics associated with MLD changes.

The MLD is an important oceanographic parameter for various practical applications including heat budget calculations. For example, the mixed layer is the layer that responds most quickly and directly to the atmospheric fluxes, and it is through this layer that such influences are transmitted to the whole ocean in the long term. The incoming heat is distributed in the entire mixed layer. Therefore, MLD is important for calculating the heat budget. Additionally, Co2 exchange takes place through this layer. Accurate estimation of MLD is crucial to understand the extent and rate of Co2 exchange, which can further research into understanding global warming, for example.

Further, sonic layer depth can be estimated using the MLD, which can be advantageous in ship navigation.

Additionally, accurate estimation of MLD is important to determine the region of entrainment processes, for example.

Figure 11:
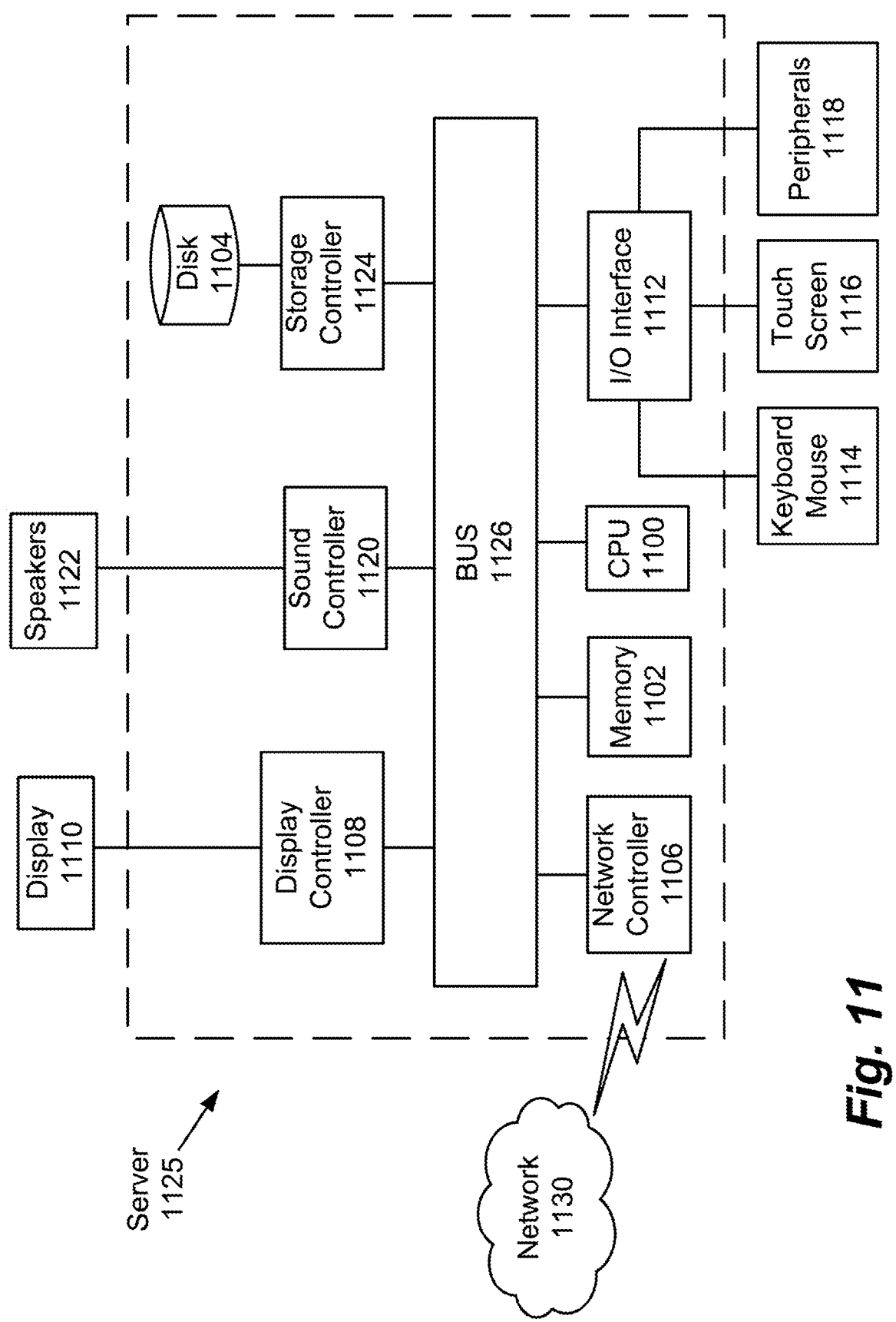
FIG. 11 is a hardware block diagram of a server according to one or more exemplary aspects of the disclosed subject matter.

Next, a hardware description of a computer/device (e.g., a server 1125) according to exemplary embodiments is described with reference to FIG. 11. In FIG. 11, the server 1125 includes a CPU 1100 which can perform one or more of the processes described herein (e.g., method of FIG. 10). The process data and instructions may be stored in memory 1102. These processes and instructions may also be stored on a storage medium disk 1104 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 1125 communicates, such as a server or computer.

Further, the claimed advancements may be provided as a utility application, background daemon, or component of an operating system, or combination thereof, executing in conjunction with CPU 1100 and an operating system such as Microsoft Windows, UNIX, Solaris, LINUX, Apple MAC-OS and other systems known to those skilled in the art.

The hardware elements in order to achieve the server 1125 may be realized by various circuitry elements. Further, each of the functions of the above described embodiments may be implemented by circuitry, which includes one or more processing circuits. A processing circuit includes a particularly programmed processor, for example, processor (CPU) 1100, as shown in FIG. 11. A processing circuit also includes devices such as an application specific integrated circuit (ASIC) and conventional circuit components arranged to perform the recited functions.

In FIG. 11, the server 1125 includes a CPU 1100 which can perform the processes described above. The server 1125 may be a general-purpose computer or a particular, special-purpose machine. In one embodiment, the server 1125 becomes a particular, special-purpose machine when the processor 1100 is programmed to perform network performance testing (and in particular, any of the processes discussed with reference to FIGS. 3 and 4).

Alternatively, or additionally, the CPU 1100 may be implemented on an FPGA, ASIC, PLD or using discrete logic circuits, as one of ordinary skill in the art would recognize. Further, CPU 1100 may be implemented as multiple processors cooperatively working in parallel to perform the instructions of the inventive processes described above.

The server 1125 in FIG. 11 also includes a network controller 1106, such as an Intel Ethernet PRO network interface card from Intel Corporation of America, for interfacing with network 1130. As can be appreciated, the network 1130 can be a public network, such as the Internet, or a private network such as an LAN or WAN network, or any combination thereof and can also include PSTN or ISDN sub-networks. The network 1130 can also be wired, such as an Ethernet network, or can be wireless such as a cellular network including EDGE, 3G and 4G wireless cellular systems. The wireless network can also be WiFi, Bluetooth, or any other wireless form of communication that is known.

The server 1125 further includes a display controller 1108, such as a graphics card or graphics adaptor for interfacing with display 1110, such as a monitor. A general purpose I/O interface 1112 interfaces with a keyboard and/or mouse 1114 as well as a touch screen panel 1116 on or separate from display 1110. General purpose I/O interface also connects to a variety of peripherals 1118 including printers and scanners.

A sound controller 1120 is also provided in the server 1125 to interface with speakers/microphone 1122 thereby providing sounds and/or music.

The general purpose storage controller 1124 connects the storage medium disk 1104 with communication bus 1126, which may be an ISA, EISA, VESA, PCI, or similar, for interconnecting all of the components of the server 1125. A description of the general features and functionality of the display 1110, keyboard and/or mouse 1114, as well as the display controller 1108, storage controller 1124, network controller 1106, sound controller 1120, and general purpose I/O interface 1112 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numer- ous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

Examples

To get a more accurate way for MLD identification, a modified form of curvature method is developed, called segment method. Segment method of MLD estimation and its advantages over other methods are discussed below.

Segment method. Segment method detects MLD by selecting a portion of profile called "profile segment" which is in between surface (i.e., surface of the body of water) and the bottom of thermocline, where the MLD should be identified. Standard deviation and gradient of the variable are used to fix upper and lower limits of profile segment. At first, the bottom and top end of profile segment are calculated. Then the closest level to MLD is fixed by analyzing the profile segment. Detailed explanation of procedure based on temperature profile (T) is given below:

a) Identifying profile segment. Profile segment, a portion of the profile within the surface and thermocline, is fixed as follows:

Gradient at i-th level ($g_T(i)$) with respect to a level 5 m deeper and curvature ($c_T(i)$) are calculated at each level as in Lorbacher et al. $\sigma_{30}(i)$ is the standard deviation of T over the levels in a 30 m interval below the i-th level. $\sigma_{10}$ is defined similar to $\sigma_{30}$, but for deeper 10 m interval. $\sigma_{30}$ and $\sigma_{10}$ represent the homogeneity of the profile. Following Lorbacher et al., and analyzing profiles at various parts of the region, a profile is assumed to have significant variability if $\sigma_{30}$ exceed 0.02 at any depth, and then the profile is considered for MLD estimation. FIG. 1 shows a typical profile of the region and MLD identification procedure. Identification of profile segment consists of two parts as describe below.

Local maxima of ($\sigma 30$) represent the regions of strong gradients. Maximum of $\sigma_{30}$ ($\sigma_{30max}$) is usually located at or near thermocline (denoted by P1 in FIG. 1). The bottom end of profile segment, $Z_{sbot}$ is the level 30 m deeper to the level of $\sigma_{30max}$ (denoted by P2 in FIG. 1). Starting point of the homogeneous layer of the profile segment is called as $Z_{stop}$. For ideal profiles, $Z_{stop}$ will be first depth near to the surface. But for profiles with short term intrusion (or gradient) within the mixed layer, the very first depth after short term intrusion is considered as $Z_{stop}$. To fix $Z_{stop}$, derived variables $\sigma_{30}$ & $\sigma_{10}$ are used. The first occurrence where $\sigma_{30} \frac{1}{4} * \sigma_{30max}$ is found (denoted by P3 in FIG. 1). Minima in $\sigma_{30}$ curve represents nearly homogeneous levels of water. Initially, the local minimum which is shallower and nearest to P3 is identified (denoted by P4 in FIG. 1). To confirm homogeneity of the region, the variability of $\sigma_{10}$ is analyzed in the lower 10 meters of water. Depth at which $\sigma_{10}$ is very low (less than 5% of $\sigma_{30max}$) with a minimum value of $\sigma_{10}$ is considered as $Z_{stop}$ (denoted by P5 in FIG. 1). The portion of profile between $Z_{stop}$ and $Z_{sbot}$ is named as "profile segment".

b) Analyzing the profile segment and identifying the level closest to MLD ($Z_{imid}$). The profile is analyzed from $Z_{stop}$ to bottom to find the closest level to MLD. At First, the shallowest depth where $|g_T(i)|>0.25*max|g_T|$ and $\alpha 30(i) >0.02$ is identified (represented as $Z_{imld0}$ and denoted by P6 in FIG. 1). The second criterion makes sure that, estimated MLD is at a location with significantly inhomogeneous deeper levels. Usually $Z_{imld0}$ is found at shallower end of the thermocline and below MLD.

Standard deviation of $g_T$ at interval $[Z_{stop}, Z_{imld0}]$, (denoted as $\sigma_{gt}$) denotes range of variability in the interval. Following Lorbacher et al., closest level to MLD also denoted by P7 in FIG. 1) is the shallowest depth where minima/maxima of the curvature falls together with positive/negative gradient $g_T$. In addition to this, two conditions are also applied to confirm MLD. Firstly $|g_T|>\sigma_{gt}$, which assures a threshold for significant local inhomogeneity in the profile. Secondly $\sigma_{30}(i)>0.02$, that confirms that the level identified is above the region of rapid changes. In other words, after defining the $Z_{imld0}$ and $Z_{stop}$, then the portion of profile between these two depths can be analyzed. Standard deviation of gradient, $g_T$, at this portion is denoted by $\sigma_{gt}$. The shallowest depth where maxima/minima of curvature fall together with positive/negative gradient can be identified. If this depth accepts the following two conditions, then the identified depth can be called $Z_{imid}$ or MLD. The two conditions include $|g_T|>\sigma_{gt}$, which assures a threshold for significant local inhomogeneity in the profile, and $\sigma_{30}(i)>0.02$, which confirms that the level identified is above the region of rapid changes. For low resolution profiles, it is recommended to apply interpolation to get more precise MLD. Interpolation process applied in Lorbacher et al. can be used, for example. If no extreme value is found in the profile segment, then the first level where $|g_T|\geq 0.7*max|g_T|$ is considered as MLD. Such MLDs are flagged in the algorithm. None of the profiles of both winter and summer season faced this situation. A flowchart showing the steps of MLD estimation procedure is given in the supporting information section (S1 File).

Mixed Layer Depth Based on Conventional Methods

Conventional methods are used to identify MLD of the region in both winter and summer using temperature and density profiles from REDSOX experiment. FIG. 2 shows the estimated MLD using threshold (with common threshold criteria for temperature, 0.2° C.), gradient (with common gradient criteria 0.025° C.) and curvature method.

Estimated mean MLD using common temperature threshold (FIGS. 2A and 2B) during winter and summer are respectively 35 m and 15 m, with minimum 11 m (10 m) and maximum 102 m (39 m) in winter (summer). Temperature and density profiles are used in the analysis and the results for both are similar. Hereafter, if not specified, statistical parameters like mean, maximum, bias, correlation coefficient, etc. are explained based on temperature profile only. FIGS. 2C and 2D shows estimated MLD in the region using the gradient method with a gradient of 0.025° C. Obtained mean MLD with gradient approach is 65 m (22 m) in winter (summer), with minimum 29 m (10 m) and maximum 116 m (50 m). MLD based on curvature method (FIGS. 2E and 2F) show mean MLD as 47 m (20 m) with the minimum at 12 m (10 m) and maximum at 111 m (47 m) in winter (summer). MLD values based on threshold, gradient and curvature methods differ from each other at many locations.

Mixed Layer Depth Based on Segment Method

Above approaches (FIG. 2) showed considerable differences in estimated MLD in both winter and summer. Close observation of individual profiles and corresponding MLD values revealed the limitations of each method. Temperature based estimates of MLD using threshold, gradient, curvature and segment based approaches for four sample stations are shown in FIG. 3. Profile I & III are during winter and II & IV are during summer.

MLD for the station I, using threshold approach is approximately between 50 to 70 m, and with gradient method is around 45 m. It is interesting that both curvature and segment methods detect MLD at 48 m. MLD observed at station II with all threshold and gradient criterions are between 20 to 30 m while curvature and segment methods detect at the same depth.

In the case of profile at station III, for lower criterions threshold method and gradient method define MLD between ~20 to ~30 m while at ~90 m for the remaining. Curvature method defines at 15 m and segment method defines at 81 m. Segment method based MLD is nearly five times greater compared to curvature based MLD. For Profiles at station IV, threshold method detects between ~10 m to ~55 m while almost all of the gradient criterions detect MLD around 11 m. Curvature method defines MLD at 11 m for temperature, whereas segment method defines at ~55 m. Considering profiles at stations I and II, it is to be noted that most of the criterions detect MLD at nearby (<5 m difference) levels, which implies these are applicable for profiles having nearly ideal structure. But in the case of profiles at stations like III and IV, detected MLD by different methods has a substantial difference from one another. For some profiles, such differences are many times larger than the other.

Differences and Limitations of Conventional Methods

The differences in estimated MLD between conventional methods and segment method are shown in FIG. 4. Difference between MLDs shows spatio-temporal variability at most of the stations. Number of stations having higher difference is more in winter than in summer. Most of the stations at the western part of gulf experienced large differences. MLD estimates based on curvature method show small differences at relatively large number of stations, especially during summer. Generally, higher extreme criterions showed overestimation while lower extremes resulted in underestimation (FIG. 3).

To analyze the performance of MLD estimation, Lorbacher et al. selected 500 profiles from various parts of the world and manually compared their method to threshold method. Similarly best MLD from four methods (threshold, gradient, curvature, and segment), are compared with a visually defined MLD (fixed by manual observation of each profile, hereafter VMLD). VMLD is the bottom of visibly quasi-homogeneous upper layer with a rapidly varying lower water column. Quality index (described in the next section) is used to confirm the reliability and accuracy of VMLD.

Number of stations available in each grid has a significant spatial difference with relatively higher number of stations in western part of analyzed area (FIG. 2). Statistical analysis for all profiles may represent the region with the higher number of profiles (west GA). Keeping this in mind, randomly selected one profile for every 0.25° *0.25° bin and are used for comparison.

Quality index. Quality index is prepared based on the notion that MLD is the bottom of nearly-homogeneous surface layer followed by a rapidly varying lower layer. Standard deviation of the variable from surface to MLD is expected to be nearly zero and that of deeper levels substantially high. Lorbacher et al. estimated quality index at arbitrary depths D1 and D2 (FIG. 5A) as:

$$QI_L = 1 - \frac{c}{c'} = 1 - \frac{\sigma(T_i - T_{mean}) \mid (z1, MLD)}{\sigma(T_i - T_{mean}) \mid (z1, 1.5 * MLD)} \qquad (1)$$

where $\sigma$ denotes standard deviation with respect to vertical mean from nearest surface depth (z1) to MLD or 1.5*MLD. Letters c & c' (portion of the profile used to calculate $\sigma$) represented by a & a' at D1 and b & b' at D2. Based on $QI_L$, quality of MLD is categorized into three: 1—"well-defined" ($QI_L>0.8$), 2—"uncertainty present" ($QI_L$ between 0.5 and 0.8) and 3—"no direct interpretation possible" ($QI_L<0.5$).

$QI_L$ has been applied on profiles to get the accuracy of MLD estimation. It has been found that $QI_L$ satisfactorily estimates the quality of MLD for most of the profiles. In some cases where the profiles have short range gradient within the mixed layer, $QI_L$ is found to have higher value for bad MLD estimates also. To overcome this limitation a new (additional) quality index is provided herein. The additional quality index ($QI_N$) is defined at arbitrary depths D1 and D2 (FIG. 5B) as:

$$QI_N = 1 - \frac{c}{c'} = 1 - \frac{\sigma(T_i - T_{mean}) \mid (MLD - 15m, MLD)}{\sigma(T_i - T_{mean}) \mid (MLD + 10m, MLD + 25m)}, \qquad (2)$$

where a is calculated for 15 m water column just above (b) and 10 m below (b') of MLD as shown in FIG. 5B. A 10 m gap is kept between b and b' to keep away the short range gradient (if any present) from calculation. FIG. 5 shows schematic diagram of quality index calculation at two arbitrary depths, which selected to compare the performance of quality index, a very shallow depth ($D_1$ at 15 m) and a more realistic depth where MLD is expected ($D_2$ at 82 m).

The corresponding values of $QI_L$ and $QI_N$ at depth D1 are 0.7 and 0.21 while at depth D2 are 0.91 and 0.99. The values of $QI_L$ and $QI_N$ are high at depth D2, indicating good quality of MLD estimation. But at D1, $QI_L$ is relatively high (close to 0.8) and $QI_N$ is very small, where small values are expected. The unexpected high value of $QI_L$ is due to the presence of short range gradient at depth D1. Quality of MLD estimation is determined by considering both $QI_L$ and $QI_N$. $QI_N<0.8$ indicates the presence of inhomogeneity in the upper layer. If both $QI_L$ and $QI_N$ are $\geq 0.8$, then defined MLD assumed to be "well-defined". The values of quality index and corresponding quality category are tabulated in Table 1.

Out of the VMLD defined profiles, 86% come under the well-defined category with $QI_L \geq 0.8$ and $QI_N \geq 0.8$, while the rest have $QI_L \geq 0.7$ and $QI_N \geq 0.8$. VMLDs that come under well-defined category are only used for comparison, to guarantee higher accuracy and reliability on manually defined VMLD.

TABLE 1

Quality category and corresponding values of $QI_L$ and $QI_N$.

| | $QI_N$ | $QI_L$ | Quality category |
|---|---|---|---|
| 1 | ≥0.8 | ≥0.8 | Well defined |
| | | 0.5-0.8 | Acceptable MLD |
| | | <0.5 | No direct interpretation possible |
| 2 | 0.5-0.8 | ≥0.8 | Uncertainty present |
| | | <0.8 | No direct interpretation possible |
| 3 | <0.5 | Any | No direct interpretation possible | doi: 10.1371/journal.pone.0165136.t001

Comparison of methods. The difference between VMLD and method based MLD is analyzed over the region. Since the mixed layer is thicker in winter than summer, difference between VMLD and method based MLD are larger in winter than in summer. Analyses discussed in this section are based on winter profiles only. Summer profiles also produced similar results, but are weaker than those in winter.

Statistical parameters computed for threshold, gradient, curvature and segment based approaches against VMLD are shown in FIG. 6 and described below. Temperature thresholds varying from 0.1° C. to 1.0° C. were used. All of the selected thresholds are found to be significantly biased. Common temperature threshold used in threshold method is 0.2° C., which showed very weak correlation (FIG. 6A). About 61% of profiles showed 25 m or more bias, of them 30% have >50 m bias. For 49% of profiles, the detected MLD is just half or less than that of VMLD. Higher thresholds examined also failed to identify realistic MLD in many cases with overestimation. For a threshold of 1.0° C. (the highest of the selected thresholds and 5 times greater than commonly used 0.2° C.), approximately 25% and 21% of profiles show a bias of 15 m and 25 m respectively. All of the thresholds are weakly correlated with VMLDs. Lower thresholds are well scattered (SI>0.5) and scattering gradually decreased to higher threshold end (SI<0.2). Observed bias is greater than the detected MLD itself for 50% of profiles at lower thresholds and close to 20% at higher thresholds.

Threshold method is strongly depended on chosen criterion. As threshold becomes larger, detected mixed layer becomes deeper (FIG. 3D). In conditions where the vertical gradient is low, detected MLD for different thresholds turn out to be significantly separated to each other and stickier in the opposite case. Similarly for two profiles with similar mixed layer, depending on the surface property value (for example SST) the identified MLD can be different. Profile with lower SST will show deeper MLD in such condition. Compared to segment method, threshold method has a poor estimation of MLD.

Gradient method has strong bias with respect to VMLD at lower gradients and becomes weaker at higher gradients. Gradient 0.03° C. is the least scattered among examined 10 gradients with a correlation of 0.66. Even though, at this gradient, 24% of profiles have a minimum 15 m bias. For the commonly used gradient (0.025° C.), 31% have a 15 m difference with low correlation (0.58). Gradients≥0.03° C. are relatively better correlated to VMLD estimates, but nearly 30% of profiles show at least 15 m bias for all gradient thresholds. The analysis shows gradient method is better than threshold method, but still has considerable weaknesses.

Similar to threshold method, gradient method also shows strong dependence on chosen gradient criterion. Other than that, in regions with small intrusion or short scale gradient in the profiles, gradient method detects MLD at such depths in most cases, which leads to large differences between detected and actual mixed layer. It strongly indicates the ineffectiveness of gradient method for GA region.

In curvature method, 40% of profiles show a bias of 25 m or higher while about 13% show 50 m bias. For nearly 28% of profiles, the detected MLD is just half of or lesser than that of VMLD. Curvature method is weakly correlated (0.38) to VMLD estimates. Dynamically active regions may possess short range gradients within the mixed layer itself. In such circumstances, curvature method identifies MLD at short gradient depths, which often leads to early detection of MLD.

MLD estimates based on segment method have strong correlation (R=0.95) and least scattering (SI=0.02). Gradient criterion 0.03° C. also has similar value for SI but shows significant bias. In the case of segment method, among the whole used profiles only 4% has a bias of 15 m or more. Detected bias for 91% of profiles is 5 m or less. Out of the 22 methods used (10 based on threshold, 10 based on gradient, 1 based on curvature and 1 based on segment), segment method is the least biased, least scattered and best correlated.

Segment method detects MLD at realistic depth and is quite helpful in avoiding short range gradients or small scale intrusions, which are present in many profiles. Segment method is free from dependence on property value at the reference depth, it is quite easy to implement to any region. For methods like threshold and gradient, it is necessary to change chosen criterion with characteristics of the region. Having no such requirement and its ability to overcome short range gradient makes segment approach more acceptable.

In the case of profiles having ideal structures, with no significant small scale gradients within the mixed layer, all the methods identify nearly equal MLDs (FIG. 3B). Many of profiles in GA have short range gradient at near surface depth with quite uniform characteristic layer beneath, followed by a clearly visible thermocline. For this reason segment based approach is used for MLD estimation in GA.

MLD Pattern in the Gulf of Aden

Segment method is used to define MLD in the region using all available temperature profiles from CTDs during winter (December-March) and summer (June-September) months, shown in FIG. 7. Maximum MLD over the region during winter (summer) is 120 m (60 m) at far west (central part) and the minimum is 22 m (10 m) at far east (west and east) with mean 77 m (21 m).

During winter, western GA has deeper mixed layer and becomes shallower to the eastern side (FIGS. 7 and 8). Mean MLDs in western, central and eastern parts of gulf are 83 m, 57 m and 49 m respectively. Shallowing tendency of MLD towards east exists in summer also, but is weak (mean MLDs are 20 m, 42 m and 17 m in west, central and east respectively). The mixed layer is shallow at western and eastern part of the gulf with deeper mixed layer at central part. Average MLD calculated along the axis of GA (along the straight line from 11.75N & 43E to 13.25N & 51.5E and meridionally averaged for +/−0.5 degrees) for winter and summer months of the year 2001 (the year with the largest number of observation) is shown in FIG. 8. MLD along the central axis follows the general spatial pattern with higher values towards west and lower towards east.

GA experiences frequent cyclonic and anti-cyclonic eddies. Bower et al. found the presence of three eddies, two cyclonic and one anti-cyclonic using ADCP current measurements. See Bower A S, Fratantoni D M, Johns W E, Peters H. Gulf of Aden eddies and their impact on Red Sea Water. Geophys Res Lett. 2002; 29: 2025. doi: 10.1029/2002GL015342, incorporated herein by reference in its entirety. Sea Level Anomalies from AVISO are shown in FIG. 9 for two days respectively in winter and summer. Al-Saafani et al. confirmed the westward movement of eddies in the region. See Al-Saafani M a., Shenoi SSC, Shankar D, Aparna M, Kurian J, Durand F, et al. Westward movement of eddies into the Gulf of Aden from the Arabian Sea. J Geophys Res Ocean. 2007; 112: 1±12. doi: 10.1029/2006JC004020, incorporated herein by reference in its entirety. Multiple numbers of eddies and movement towards the west lead to complex dynamics in the region. During winter, south of the western GA has relatively shallower (~75 m) MLD than that of north (~110 m), which can be related to observed cyclonic eddy at south of the western part (FIG. 9A). Similarly, east of 48° E has deeper MLD than the surrounding region. Presence of the anti-cyclonic eddy centered at 49° E might have deepening effect on MLD of the region. Cyclonic eddy at central part of the gulf also showed its signature in the MLD pattern with lower MLD values. In summer, MLD gradually becomes shallow from west to east, with abnormally deeper MLD at central part of the gulf (FIG. 8). An anti-cyclonic eddy has existed at central gulf from June (figure not shown). This eddy intensified during July and continued until middle of August (FIG. 9B), which might have significantly influenced mixing in the region and resulted in a deeper mixed layer.

MLD detected by conventional methods is analyzed in Gulf of Aden region. Threshold and gradient methods were applied on temperature profiles with commonly used criterion 0.03 kg m$^{-3}$ and 0.005 kg m$^{-3}$ m$^{-1}$, and underestimate MLD by 20 m for ~50% of profiles in the Gulf of Aden region. Lower and higher extreme criterions used also failed to capture reliable depth of mixed layer with under or over estimation. For profiles with more or less ideal shape, all techniques estimated MLD with an acceptable difference of <5 m. In such conditions, curvature method exhibited higher efficiency than threshold and gradient methods. For profiles with irregular shape, conventional methods are unable to identify realistic MLD due to the presence of short range gradients within the mixed layer itself. Segment method of MLD estimation overcomes major limitations of conventional methods. Curvature and segment methods have two key advantages over threshold and gradient method, i.e. they are independent of the property value at the surface like SST, and estimated MLD is free from linear dependence on the used threshold or gradient criterion. In addition, segment method overcomes limitations of short-range gradient or small scale intrusion that may be present in highly dynamic regions. These advantages of segment method make it more reliable and acceptable. Quality index definition is useful to confirm the accuracy and reliability of estimated MLD.

Detected MLD by segment method is used to show temporal and spatial variability of mixed layer structure. Generally, in both, winter and summer, the western part of gulf has deeper mixed layer and shallows gradually to the east (FIGS. 7 and 8). SLA of the region confirms the presence of cyclonic and anti-cyclonic eddies in the region. Eddies in the region influence water up to 1000 m and more and play significant role in mixed layer changes of the region. Deeper mixed layer at the central part of gulf during summer, against the general pattern, is due to the relatively strong anti-cyclonic eddy in the region during this period (FIG. 9B). Due to complex nature of the region, detailed investigation on the influence of eddies and other parameters are essential to formulate a clear picture of dynamics associated with MLD changes.

The invention claimed is:

1. A method, comprising:
reading, via processing circuitry of an oceanographic device, a vertical high resolution profile corresponding to a body of water, the vertical high resolution profile including temperature and salinity of the body of water;
determining, via the processing circuitry of the oceanographic device, whether intervals of the vertical high resolution profile are inhomogeneous or nearly homogeneous water columns;
only when said determining determines that the intervals of the vertical high resolution profile are inhomogeneous, performing the following operations:
selecting, via the processing circuitry of the oceanographic device, a profile segment corresponding to a portion of the vertical high resolution profile between a surface of the body of water and a bottom of a thermocline, said selecting the profile segment including:
determining, via the processing circuitry of the oceanographic device, a fixed upper limit ($Z_{stop}$) of the profile segment calculated based on a standard deviation and gradient of temperature throughout the vertical high resolution profile, and
determining, via the processing circuitry of the oceanographic device, a fixed lower limit ($Z_{sbot}$) of the profile segment calculated based on the standard deviation and gradient of temperature throughout the vertical high resolution profile;
identifying, via the processing circuitry of the oceanographic device, a shallowest depth ($Z_{imld}$) in the selected profile segment where the following three conditions are satisfied:
(1) minimum/maxima of curvature fall together with positive/negative gradient ($g_T$),
(2) $|g_T(i)|>\sigma_{g_t}$, where $g_T(i)$ is the gradient at a predetermined interval (i), $\sigma_{g_t}$ is the standard deviation of gradient between $Z_{stop}$ and $Z_{imld0}$, and
(3) $\sigma_{30}(i)>0.02$, where $\sigma_{30}(i)$ is the standard deviation of temperature in Celsius in a 30 meter interval below a current depth,
otherwise, when the three criteria are not satisfied, approximate the shallowest depth within the selected profile segment at which $g_T>0.7*\max|g_T|$;
setting, via the processing circuitry of the oceanographic device, as corresponding to the mixed layer depth, the identified shallowest depth or the approximated shallowest depth depending upon whether or not the three criteria are satisfied;
outputting, on a display device of the oceanographic device, using the processing circuitry of the oceanographic device, a graphic identification of the corresponding set mixed layer depth in the form of a flag on a graph;
estimating a sonic layer depth based on the set mixed layer depth; and
navigating a ship based on the sonic layer depth.

2. The method of claim 1, wherein the vertical high resolution profile has a resolution of 1 meter.

3. The method of claim 1, further comprising:
determining when $|g_T|>\sigma_{g_t}$ to ensure a threshold for significant local inhomogeneity in the vertical high resolution profile, wherein $\sigma_{g_t}$ corresponds to the standard deviation of $g_T$ at an interval corresponding to [$Z_{stop}$, $Z_{imld0}$].

4. The method of claim 3, further comprising:
determining when $\sigma_{30}(i)>0.02$ to confirm that the depth identified as the mixed layer depth is above an interval or rapid changes in temperature in Celsius.

* * * * *